United States Patent
Crofoot et al.

(10) Patent No.: US 10,357,445 B2
(45) Date of Patent: Jul. 23, 2019

(54) CROSS-LINKED COMPOSITION AND COSMETIC COMPOSITION COMPRISING THE SAME

(71) Applicant: Dow Corning Corporation, Midland, MI (US)

(72) Inventors: Mary Kay Crofoot, Midland, MI (US); Roxanne Haller, Saginaw, MI (US); Donald Anthony Kadlec, Midland, MI (US); Kimmai Thi Nguyen, Midland, MI (US); Kenneth Edward Zimmerman, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/306,186

(22) PCT Filed: Apr. 24, 2015

(86) PCT No.: PCT/US2015/027579
§ 371 (c)(1),
(2) Date: Oct. 24, 2016

(87) PCT Pub. No.: WO2015/167963
PCT Pub. Date: Nov. 5, 2015

(65) Prior Publication Data
US 2017/0065514 A1    Mar. 9, 2017

Related U.S. Application Data

(60) Provisional application No. 61/984,966, filed on Apr. 28, 2014, provisional application No. 62/017,570, filed on Jun. 26, 2014.

(51) Int. Cl.

| | |
|---|---|
| A61K 8/891 | (2006.01) |
| A61K 8/91 | (2006.01) |
| A61Q 19/00 | (2006.01) |
| A61Q 5/00 | (2006.01) |
| A61Q 5/02 | (2006.01) |
| A61Q 5/12 | (2006.01) |
| C08G 77/38 | (2006.01) |
| C08L 83/06 | (2006.01) |
| A61K 8/81 | (2006.01) |
| A61K 8/894 | (2006.01) |
| A61Q 1/06 | (2006.01) |
| A61Q 15/00 | (2006.01) |
| A61Q 19/10 | (2006.01) |
| C08K 5/01 | (2006.01) |
| C08K 5/092 | (2006.01) |

(Continued)

(52) U.S. Cl.
CPC ............ *A61K 8/891* (2013.01); *A61K 8/8147* (2013.01); *A61K 8/894* (2013.01); *A61Q 1/06* (2013.01); *A61Q 5/00* (2013.01); *A61Q 5/02* (2013.01); *A61Q 5/12* (2013.01); *A61Q 15/00* (2013.01); *A61Q 19/00* (2013.01); *A61Q 19/10* (2013.01); *C08G 77/38* (2013.01); *C08K 5/01* (2013.01); *C08K 5/092* (2013.01); *C08K 5/56* (2013.01); *C08L 83/06* (2013.01); *A61K 2800/10* (2013.01); *A61K 2800/594* (2013.01); *C08G 77/12* (2013.01); *C08G 77/14* (2013.01)

(58) Field of Classification Search
CPC .................................................. A61Q 19/00
See application file for complete search history.

(56) References Cited

U.S. PATENT DOCUMENTS

| | | |
|---|---|---|
| 4,987,169 A | 1/1991 | Kuwata et al. |
| 5,241,034 A | 8/1993 | Herzig et al. |

(Continued)

FOREIGN PATENT DOCUMENTS

| | | |
|---|---|---|
| CA | 2483911 A1 | 11/2003 |
| CA | 2510428 A1 | 7/2004 |

(Continued)

OTHER PUBLICATIONS

PCT/US2015/027579 International Search Report dated Jul. 15, 2015, 4 pages.
English language abstract and machine translation for WO0000559 (A1) extracted from http://worldwide.espacenet.com database on Sep. 13, 2017, 29 pages.
English language abstract and machine translation for JP2011026498 (A) extracted from http://worldwide.espacenet.com database on Sep. 13, 2017, 37 pages.
English language abstract and machine translation for JP2002194220 (A) extracted from http://worldwide.espacenet.com database on Sep. 13, 2017, 21 pages.

(Continued)

*Primary Examiner* — Kyle A Purdy
(74) *Attorney, Agent, or Firm* — Warner Norcross & Judd LLP

(57) ABSTRACT

A cross-linked composition comprises the reaction product of an organohydrogensiloxane and a cross-linker, in the presence of a hydrosilylation catalyst. The organohydrogensiloxane comprises siloxy units of average formula (I): $(R^4{}_3SiO_{1/2})(R^4{}_2{-}SiO_{2/2})_a(R^1R^4SiO_{2/2})_b(R^4HSiO_{2/2})_c(R^2R^4SiO_{2/2})_d(R^3R^4SiO_{2/2})_e{-}(R^4{}_3Si{-}O_{1/2})$. Each of $R^1$ and $R^2$ is an independently selected hydrogen atom or a substituted or unsubstituted hydrocarbyl group. $R^3$ is a hydrogen atom or a group having at least one carboxyl group or a precursor thereof. $R^4$ is an independently selected substituted or unsubstituted hydrocarbyl group. Further, $a \geq 0$, $b \geq 0$, $c \geq 1$, $d \geq 0$, and $e \geq 1$. The cross-linker has at least two aliphatic unsaturated hydrocarbon groups. A method of forming the cross-linked composition comprises the steps of providing the organohydrogensiloxane and cross-linker, and combining the organohydrogensiloxane and cross-linker in the presence of the hydrosilylation catalyst to form the cross-linked composition. A cosmetic composition is provided that includes the cross-linked composition and at least one cosmetic component.

15 Claims, No Drawings

(51) Int. Cl.
*C08K 5/56* (2006.01)
*C08G 77/12* (2006.01)
*C08G 77/14* (2006.01)

(56) References Cited

U.S. PATENT DOCUMENTS

| | | | |
|---|---|---|---|
| 5,332,796 | A | 7/1994 | Yoshikawa et al. |
| 5,386,007 | A | 1/1995 | Herzig et al. |
| 5,444,139 | A | 8/1995 | Valpey, III et al. |
| 5,654,362 | A | 8/1997 | Schulz, Jr. et al. |
| 5,760,116 | A | 6/1998 | Kilgour et al. |
| 5,919,441 | A | 7/1999 | Mendolia et al. |
| 5,981,680 | A | 11/1999 | Petroff et al. |
| 6,051,216 | A | 4/2000 | Barr et al. |
| 6,709,752 | B1 | 3/2004 | James et al. |
| 7,388,049 | B2 | 6/2008 | O'Brien |
| 8,026,330 | B2 | 9/2011 | Kamei |
| 8,147,854 | B2 | 4/2012 | Okawa et al. |
| 8,273,840 | B2 | 9/2012 | Lin |
| 8,398,964 | B2 | 3/2013 | Kamei et al. |
| 8,703,881 | B2 | 4/2014 | Saxena et al. |
| 8,772,422 | B2 | 7/2014 | Saxena et al. |
| 9,486,652 | B2 | 11/2016 | Araki et al. |
| 9,822,221 | B2 * | 11/2017 | Kadlec .................. C08G 77/54 |
| 2002/0061969 | A1 | 5/2002 | Shiono et al. |
| 2002/0188058 | A1 | 12/2002 | Chaiyawat et al. |
| 2003/0068348 | A1 | 4/2003 | Ferrari et al. |
| 2003/0072730 | A1 | 4/2003 | Tournilhac |
| 2003/0170188 | A1 | 9/2003 | Ferrari et al. |
| 2003/0235553 | A1 | 12/2003 | Lu et al. |
| 2004/0039132 | A1 | 2/2004 | Ferritto et al. |
| 2004/0044121 | A1 | 3/2004 | Kadlec et al. |
| 2004/0180032 | A1 | 9/2004 | Manelski et al. |
| 2004/0236054 | A1 | 11/2004 | George et al. |
| 2008/0254076 | A1 | 10/2008 | Ferrari et al. |
| 2009/0252774 | A1 | 10/2009 | Kamei et al. |
| 2009/0253885 | A1 | 10/2009 | Kamei |
| 2010/0190871 | A1 | 7/2010 | Araki et al. |
| 2010/0330011 | A1 | 12/2010 | Kennan et al. |
| 2011/0027213 | A1 | 2/2011 | Kamei et al. |
| 2011/0172345 | A1 | 7/2011 | Goto et al. |
| 2012/0040931 | A1 | 2/2012 | Kamei |
| 2016/0200876 | A1 * | 7/2016 | Kadlec .................. A61Q 19/00 528/28 |

FOREIGN PATENT DOCUMENTS

| | | |
|---|---|---|
| CN | 1612918 A | 5/2005 |
| DE | 4300809 A1 | 7/1994 |
| DE | 4300809 A1 | 7/1994 |
| EP | 0196169 A2 | 10/1986 |
| EP | 0492657 A1 | 7/1992 |
| EP | 0848029 A2 | 6/1998 |
| EP | 0869142 A2 | 10/1998 |
| EP | 1266647 A1 | 12/2002 |
| EP | 1266647 A1 | 12/2002 |
| EP | 1266648 A1 | 12/2002 |
| EP | 1266648 A1 | 12/2002 |
| EP | 1266653 A1 | 12/2002 |
| EP | 1266653 A1 | 12/2002 |
| EP | 2107078 A1 | 10/2009 |
| EP | 2418236 A1 | 2/2012 |
| JP | H05310753 A | 11/1993 |
| JP | H05310753 A | 11/1993 |
| JP | 2002105319 A | 4/2002 |
| JP | 2002105319 A | 4/2002 |
| JP | 2002194220 A | 7/2002 |
| JP | 2002194220 A | 7/2002 |
| JP | 2005503348 A | 2/2005 |
| JP | 2005503348 A | 2/2005 |
| JP | 2009263213 A | 11/2009 |
| JP | 2009263213 A | 11/2009 |
| JP | 2009263643 A | 11/2009 |
| JP | 2009263643 A | 11/2009 |
| JP | 201126485 A | 2/2011 |
| JP | 201126485 A | 2/2011 |
| JP | 2011026493 A | 2/2011 |
| JP | 2011026493 A | 2/2011 |
| JP | 2011026498 A | 2/2011 |
| JP | 2011026498 A | 2/2011 |
| JP | 2014074058 A | 4/2014 |
| JP | 2014074058 A | 4/2014 |
| JP | 2015512956 A | 4/2014 |
| JP | 2015512956 A | 4/2014 |
| JP | 2015511969 A | 4/2015 |
| JP | 2015511969 A | 4/2015 |
| KR | 1020040106509 A | 12/2004 |
| KR | 1020080023479 A | 3/2008 |
| WO | WO0000559 A1 | 1/2000 |
| WO | WO0000559 A1 | 1/2000 |
| WO | WO03105789 A1 | 12/2003 |
| WO | WO03105801 A1 | 12/2003 |
| WO | WO03106614 A2 | 12/2003 |
| WO | WO2004000247 A1 | 12/2003 |
| WO | WO2004054523 A1 | 7/2004 |
| WO | WO2004054524 A1 | 7/2004 |
| WO | WO2004060101 A2 | 7/2004 |
| WO | WO2004060271 A2 | 7/2004 |
| WO | WO2004060276 A2 | 7/2004 |
| WO | WO2007109240 A2 | 9/2007 |
| WO | WO2007109260 A2 | 9/2007 |
| WO | WO2007109282 A2 | 9/2007 |
| WO | WO2009006091 A2 | 1/2009 |
| WO | WO2010010841 A1 | 1/2010 |
| WO | WO2010010841 A1 | 1/2010 |
| WO | WO2010080755 A2 | 7/2010 |
| WO | WO2013103535 A1 | 7/2013 |
| WO | WO2013103536 A1 | 7/2013 |
| WO | WO2016014127 A1 | 1/2016 |
| WO | WO2016014128 A1 | 1/2016 |

OTHER PUBLICATIONS

Anubhav Saxena, et al. "A Systematic Approach to Decipher the Microstructure of Methyl Hydrosiloxane Copolymers and Its Impact on Their Reactivity Trends", Macromolecules 2011, 44, p. 6480-6487.

G. Rajesh, et al. "Liquid Silicone Rubber Vulcanizates: Network Structure—Property Relationship and Cure Kinetics", Polymers & Polymer Composites, vol. 18, No. 9, 2010, p. 477-488.

"Momentive Safety Data Sheet, LSR 2050", Version 1.3, Jan. 16, 2013, 6 pages.

English Abstract and machine assisted translation of JP2011026493A obtained from Espacenet on Sep. 13, 2018, 36 pages.

English Abstract and machine assisted translation of JP2015512956A obtained from Espacenet on Sep. 13, 2018, 13 pages.

* cited by examiner

CROSS-LINKED COMPOSITION AND COSMETIC COMPOSITION COMPRISING THE SAME

CROSS-REFERENCE TO RELATED APPLICATIONS

This application is the National Stage of International App. No. PCT/US2015/027579 filed on Apr. 24, 2015, which claims priority to and all advantages of U.S. Pat. App. No. 61/984,966 filed on Apr. 28, 2014 and U.S. Pat. App. No. 62/017,570 filed on Jun. 26, 2014, the contents of which are hereby incorporated by reference.

This application claims priority to and all advantages of U.S. Pat. App. No. 61/984,966 filed on Apr. 28, 2014 and U.S. Pat. App. No. 62/017,570 filed on Jun. 26, 2014, the content of which is hereby incorporated by reference.

This disclosure generally relates to a cross-linked composition comprising the reaction product of an organohydrogensiloxane and a cross-linker, and to a method of forming the cross-linked composition. This disclosure also relates to a cosmetic composition comprising the cross-linked composition and at least one cosmetic component.

Conventional silicone elastomer gels/blends ("gels") have been used extensively to enhance the aesthetics of personal care formulations by providing a unique sensory profile upon application. For example, gels can provide sensory characteristics such as a velvety, silky or powdery feel. In addition, gels are also valued for providing rheology modification to personal care and health care formulations. Unfortunately, conventional gels have limited versatility in formulations with polar solvents, such as hydrocarbon oils, ester oils and plant based oils, as well as limited compatibility with members of the fatty glyceride family or other fatty substances, such as sebum. Also, many of these gels are non-durable when used on skin.

In view of the foregoing, there remains an opportunity to provide silicone compositions with increased formulation versatility and compatibility, as well as to provide silicone compositions having excellent aesthetic and rheological properties. There also remains an opportunity to provide silicone compositions which may positively impact the sensory profile of cosmetic compositions. There is also a need to improve substantivity of silicone compositions on keratinous substrates.

BRIEF SUMMARY OF THE INVENTION

Disclosed is a cross-linked composition. The cross-linked composition comprises the reaction product of an organohydrogensiloxane and a cross-linker. The reaction product is typically formed in the presence of a hydrosilylation catalyst.

The organohydrogensiloxane comprises siloxy units of average formula (I):

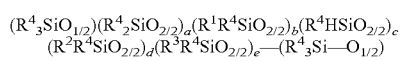

In formula (I), each of $R^1$ and $R^2$ is an independently selected hydrogen atom or a substituted or unsubstituted hydrocarbyl group. $R^3$ is a hydrogen atom or a group having at least one carboxyl group or a precursor thereof. $R^4$ is an independently selected substituted or unsubstituted hydrocarbyl group. Further, $a \geq 0$, $b \geq 0$, $c \geq 1$, $d \geq 0$, and $e \geq 1$. The cross-linker has at least two aliphatic unsaturated hydrocarbon groups.

Typically, the cross-linked composition is of the following general formula (II):

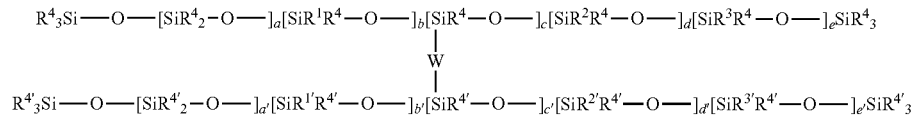

In formula (II), W is a divalent group. Each of $R^1$, $R^{1'}$, $R^2$, $R^{2'}$, $R^4$, and $R^{4'}$ is an independently selected substituted or unsubstituted hydrocarbyl group. Each of $R^3$ and $R^{3'}$ is independently a group having at least one carboxyl group or a precursor thereof. Further, $a \geq 0$, $a' \geq 0$, $b \geq 0$, $b' \geq 0$, $c \geq 1$, $c' \geq 1$, $d \geq 0$, $d' \geq 0$, $e \geq 1$, and $e' \geq 1$.

Also disclosed is a method of forming the cross-linked composition. The method comprises the steps of providing the organohydrogensiloxane and providing the cross-linker. The method further comprises the step of combining the organohydrogensiloxane and the cross-linker to form the cross-linked composition. The hydrosilylation catalyst is typically present during the step of combining.

A cosmetic composition comprising the cross-linked composition is also disclosed. The cosmetic composition further comprises at least one cosmetic component (optionally in a cosmetically acceptable medium).

The cross-linked composition has excellent formulation versatility. The cross-linked composition can also have excellent tactile aesthetic and/or rheological properties. For example, the cross-linked composition can have a dry, velvety feel, which is unmatched by conventional silicone products. The cross-linked composition can also have excellent water uptake and/or excellent compatibility with organic solvents, such as those used in personal care applications. It is thought that potential benefits provided by, or attributable to, the cross-linked composition include, but are not limited to, film forming, substantivity, durability, pigment/particle suspension and/or modification, long lasting/wear, additional chemistry, actives (e.g. drug) or inactives (e.g. fragrance) delivery/release, and combinations thereof. The cross-linked composition can also have excellent compatibility with members of the fatty glyceride family or other fatty substances such as sebum, and can also be durable when used on skin.

The cross-linked composition is useful for a variety of end applications, and is not limited to any particular one. Examples of suitable applications include use in personal care, household care, health care, and beauty care, products. In embodiments having free carboxyl groups, the cross-linked composition can also be used for modifying organic resins or fibers and surface-treating powder. The treated surface shows high affinity with an unctuous agent. Particularly, dispersivity of powder is significantly improved. Therefore, the cross-linked composition can be useful for applications where high dispersivity of a powder is required, for example, cosmetics such as skincare and makeup products, and coatings. The cross-linked composition can also be used to enhance the aesthetics of personal care formulations for skin care and health care by providing a unique sensory profile upon application. In addition, the composition can be used for providing rheology modification to personal care and health care formulations.

DETAILED DESCRIPTION

Disclosed herein are a cross-linked composition and a method of forming the cross-linked composition. In various embodiments, the cross-linked composition may also be referred to as an elastomer or a silicone elastomer. In further embodiments, the elastomer may also be referred to as a carboxyl-functional elastomer or COOH-elastomer. It is to be appreciated that the cross-linked composition may be in forms other than elastomeric, such as a fluid, semi-fluid, or gel form depending, e.g., on the amount of cross-linking, chain lengths, etc.

Also disclosed herein are cosmetic compositions that include the cross-linked composition and at least one cosmetic component. Moreover, the cosmetic compositions may optionally include a cosmetically acceptable medium. For example, the cosmetic component(s) can be in the cosmetically acceptable medium. Alternatively or in addition, the cosmetically acceptable medium can be utilized separate from the cosmetic component.

Cosmetic compositions generally include those compositions which are intended to be placed in contact with the external parts of the human body (skin e.g. epidermis), hair system, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or correcting body odors. In some instances, cosmetic compositions may also include health care compositions. Cosmetic applications, and in some instances health care applications, include skin care, sun care, hair care, or nail care applications. The cosmetic composition may also be referred to as a personal care composition.

Cross-Linked Composition

The cross-linked composition comprises the reaction product of an organohydrogensiloxane and a cross-linker. In certain embodiments, the cross-linked composition consists essentially of the reaction product of the organohydrogensiloxane and the cross-linker. In further embodiments, the cross-linked composition consists of the reaction product of the organohydrogensiloxane and the cross-linker. The reaction product is typically formed in the presence of a hydrosilylation catalyst.

The organohydrogensiloxane comprises siloxy units of average formula (I):

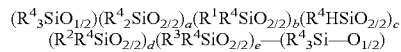

In formula (I), the siloxy units represented by subscripts a, b, c, d, and e, i.e., the groups in parentheses, may be present in any order within the siloxane, including a different order than that which is represented above and throughout this disclosure. Moreover, these groups may be present in randomized or block form.

Typically, a≥0, b≥0, c≥1, d≥0, and e≥1. In other words, the organohydrogensiloxane comprises at least one c and e, and optionally, can have one or more of each of a, b, and d. The organohydrogensiloxane can be of various molecular weights. Typically, the sum of a+b+c+d+e is an integer selected from 4-2,000, 10-1,750, 25-1,500, 25-1,000, 25-900, 25-800, 25-700, 25-600, 25-500, 25-400, 25-300, 50-200, 75-150, 85-125, or 90-110, or any number in between.

Typically, a is an integer selected from 0-1,000, 0-950, 0-750, 0-500, 0-400, 1-350, 1-300, 25-250, 50-200, 50-150, 75-125, 90-110, 90-100, or 90-95, or any number in between. Alternatively, a is an integer selected from 0-100, 0-90, 0-80, 0-70, 0-60, 1-50, 1-40, 1-30, 1-25, 1-20, 1-15, 1-10, 1-7.5, or 1-5, or any number in between.

Typically, b is an integer selected from 1-100, 1-75, 1-50, 1-25, 1-20, 1-10, or 1-5, or any number in between. Alternatively, b is an integer selected from 0-100, 0-90, 0-80, 0-70, 0-60, 0-50, 0-40, 0-30, 0-25, 0-20, 0-15, 0-10, 0-7.5, or 0-5, or any number in between.

Typically, c is an integer selected from 0-1,000, 0-950, 0-750, 0-500, 0-400, 1-350, 1-300, 1-250, 1-200, 1-150, 1-100, 1-75, 1-50, 1-25, 1-20, 1-15, 1-10, or 1-5, or any number in between. Alternatively, c is an integer selected from 0-100, 0-90, 0-80, 0-70, 0-60, 1-50, 1-40, 1-30, 1-25, 1-20, 1-15, 1-10, 1-7.5, or 1-5, or any number in between.

Typically, d is an integer selected from 1-100, 1-75, 1-50, 1-25, 1-20, 1-10, or 1-5, or any number in between. Alternatively, d is an integer selected from 0-100, 0-90, 0-80, 0-70, 0-60, 0-50, 0-40, 0-30, 0-25, 0-20, 0-15, 0-10, 0-7.5, or 0-5, or any number in between.

Typically, e is an integer selected from 1-100, 1-75, 1-50, 1-25, 1-20, 1-10, or 1-5, or any number in between. Alternatively, e is an integer selected from 0-100, 0-90, 0-80, 0-70, 0-60, 1-50, 1-40, 1-30, 1-25, 1-20, 1-15, 1-10, 1-7.5, or 1-5, or any number in between.

In various embodiments, 10≤a≤500, 0≤b≤100, 1≤c≤100, 0≤d≤100, and 1≤e≤100. In further embodiments, 255≤a≤300, 0≤b≤60, 1≤c≤60, 0≤d≤60, and 1≤e≤60. In yet further embodiments, 40≤a≤200, 0≤b≤40, 1≤c≤40, 0≤d≤40, and 15≤e≤40. Various subranges for each of a, b, c, d, and e can be utilized.

In certain embodiments, $R^1$ is a hydrogen atom, i.e. a Si—H reactive site (or silicon-bonded hydrogen atom). Such a site can be used to graft side-groups/chains of various chemistries. In other embodiments, $R^1$ is an independently selected substituted or unsubstituted hydrocarbyl group. By "substituted," it is meant that one or more hydrogen atoms of the hydrocarbon may be replaced with atoms other than hydrogen (e.g. a halogen atom), or a carbon atom within the chain of $R^1$ may be replaced with an atom other than carbon, i.e., $R^1$ may include one or more heteroatoms within the chain, such as oxygen, sulfur, nitrogen, etc. Examples of suitable hydrocarbyl groups represented by $R^1$ include alkyl, aryl, alkenyl, alkaryl, and aralkyl, groups.

$R^1$ may be a substituted or unsubstituted aliphatic or aromatic hydrocarbyl. Monovalent unsubstituted aliphatic hydrocarbyls are exemplified by, but not limited to, alkyl groups, such as methyl, ethyl, propyl, pentyl, octyl, undecyl, and octadecyl; and cycloalkyl groups, such as cyclohexyl. Monovalent substituted aliphatic hydrocarbyls are exemplified by, but not limited to, halogenated alkyl groups, such as chloromethyl, 3-chloropropyl, and 3,3,3-trifluoropropyl. Aromatic hydrocarbyls are exemplified by, but not limited to, phenyl, tolyl, xylyl, benzyl, styryl, and 2-phenylethyl.

In certain embodiments, $R^1$ is an independently selected alkyl group, aryl group, or $(R^6O)_m$ group. If $R^1$ is a $(R^6O)_m$ group, $R^6$ is typically an alkyl group or aryl group and m is an integer selected from 1-50, 1-25, 1-10, 1-5, or 1, or any number in between. The $(R^6O)_m$ group may also be referred to as a polyether group. In other embodiments, $R^1$ is an independently selected alkyl group having from 1-30, 1-25, 1-20, 1-15, 1-10, 1-6, 1-4, or 1-2, carbon atoms, or any number of carbon atoms in between. Specific examples of suitable alkyl groups as $R^1$ include methyl groups, ethyl groups, propyl groups, butyl groups, pentyl groups, etc.

Without being bound or limited by any particular theory, it is thought that the organic compatibility of the cross-linked composition, e.g. in a solvent, can be enhanced by having a long chain alkyl group on the siloxane backbone, e.g. as $R^1$. Typically, $R^1$ is either a polyether group or an alkyl group. It is also thought that the hydrophilic character of the cross-linked composition can be enhanced by having a polyether side chain (or chains) on the siloxane backbone, e.g. as $R^1$.

$R^2$ is an independently selected hydrogen atom or a substituted or unsubstituted hydrocarbyl group. Examples of suitable groups for $R^2$ are as described for $R^1$. $R^2$ can be the same as or different from $R^1$. In specific embodiments, $R^2$ is a methyl group.

$R^4$ is an independently selected substituted or unsubstituted hydrocarbyl group. Examples of suitable groups for $R^4$ are as described for $R^1$. In certain embodiments, $R^4$ is an independently selected alkyl group. The alkyl group typically has from 1-30, 1-25, 1-20, 1-15, 1-10, 1-6, 1-4, or 1-2, carbon atoms, or any number of carbon atoms in between. Typically, $R^4$ is a methyl group.

In various embodiments, each of $R^1$, $R^2$, and $R^4$ is an independently selected monovalent organic group having 1-30 carbon atoms, or any number of carbon atoms in between. In further of these embodiments, each of $R^1$ and $R^4$ is a methyl group. $R^2$ can be an aliphatic or aromatic group having from 1-12, 1-6, or 1-4, carbon atoms, or any number of carbon atoms in between. For example, $R^2$ can be a butyl, hexyl, octyl, decyl, or phenyl group. Alternatively, $R^2$ can be a methyl group.

In certain embodiments, $R^3$ is a hydrogen atom, i.e. a Si—H reactive site. If present, this Si—H reactive site is typically utilized to form a further reaction product of the cross-linked composition. In other embodiments, $R^3$ is a group having at least one carboxyl group or a precursor thereof. By "precursor," it is meant that that the group can be made or converted into a carboxyl group, e.g. via reaction, heating, etc.

In specific embodiments, $R^3$ is hydrogen atom and the cross-linked composition comprises the further reaction product of a compound that is reactive with $R^3$, i.e., with Si—H. The compound has an aliphatic unsaturated hydrocarbon group and at least one carboxyl group or a carboxyl group precursor. The aliphatic unsaturated hydrocarbon group can be an alkenyl or alkynyl group. Representative, non-limiting examples of alkenyl groups are shown by the following structures; $H_2C=CH-$, $H_2C=CHCH_2-$, $H_2C=C(CH_3)CH_2-$, $H_2C=CHCH_2CH_2-$, $H_2C=CHCH_2CH_2CH_2-$, and $H_2C=CHCH_2CH_2CH_2CH_2-$. Representative, non-limiting examples of alkynyl groups are shown by the following structures; $HC\equiv C-$, $HC\equiv CCH_2-$, $HC\equiv CC(CH_3)-$, $HC\equiv CC(CH_3)_2-$, and $HC\equiv CC(CH_3)_2CH_2-$. In certain embodiments, the aliphatic unsaturated hydrocarbon of the compound is an independently selected $C_2$-$C_{12}$ alkenyl group. Suitable alkenyl groups include vinyl, allyl, butenyl, pentenyl, hexenyl, and decenyl, groups. The alkenyl group is typically a vinyl or hexenyl group, more typically a vinyl group.

In various embodiments, the compound has at least one terminal carboxyl group. In other embodiments, the compound has at least one terminal carboxyl group precursor. For example, the carboxyl group precursor can be selected from an anhydride group or a capped (or blocked/protected) carboxyl group. Various types of compounds can be used, provided that the compound has a group that is reactive with the Si—H reactive site for linking to the siloxane backbone and another group that provides a carboxyl group or carboxyl group precursor extending from the siloxane backbone.

Suitable compounds for reaction with the Si—H reactive site include carboxylate derivatives. Examples of such compounds are described as a "trimethylsilyl carboxylate derivative having a vinyl end" in US Pub. No. 2010/0190871 to Araki et al. ("Araki"), the disclosure of which is incorporated by reference. In specific embodiments, the compound comprises trimethylsilyl undecylenate.

In related embodiments, the compound comprises trimethylsilyl undecylenate and the cross-linked composition comprises the further reaction product of an alcohol. In these embodiments, the alcohol is used to remove the trimethylsilyl group imparted by the trimethylsilyl undecylenate and provide a carboxyl group. An alcoholysis reaction of this sort is described in Araki, and heating can be used to facilitate the reaction.

Other suitable compounds for reaction with the Si—H reactive site are acid anhydrides including, but are not limited to, succinic acid anhydride and derivatives thereof, such as vinyl succinic acid anhydride, allyl succinic acid anhydride, allyl-2-methylsuccinic acid anhydride, allyl-2,3-dimethyl succinic acid anhydride, and allyl-2-ethyl succinic acid anhydride. In specific embodiments, the compound comprises allyl succinic anhydride (ASA).

In related embodiments, the compound comprises ASA and the cross-linked composition comprises the further reaction product of water, an alcohol, or a combination thereof. In these embodiments, water can be used to open the anhydride group imparted by ASA to provide two carboxyl groups. Similarly, an alcohol can be used to open the anhydride group imparted by ASA to provide a carboxyl group and an ester. Various alcohols can be utilized, e.g. monohydric alcohols, and this disclosure is not limited to a particular one. Combinations of different compounds can be utilized to provide various groups on the siloxane backbone(s) of the cross-linked composition.

In various embodiments, $R^3$ is of the following general formulas (i), (ii), (iii), or (iv):

(i)

(ii)

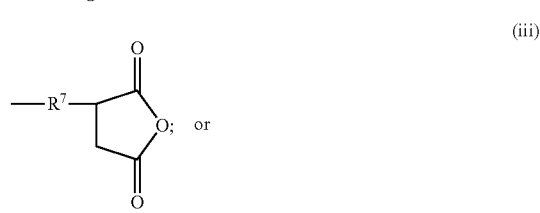

(iii)

(iv)

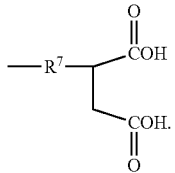

In each of these formulas, $R^7$ is a divalent group. Typically, $R^7$ is a hydrocarbylene, heterohydrocarbylene, or organoheterylene group. In various embodiments, $R^7$ is $(CH_2)_n$ where n is an integer selected from 1-30, 1-25, 1-20, 1-15, 1-10, 1-5, or 1-3, or any number in between. In certain embodiments, n is 3 or 10. In formula (ii), X can be a monovalent organic group having 1-30 carbon atoms, or any number of carbon atoms in between. Typically, X is a methyl group. The cross-linked composition can include a combination of different $R^3$ groups, e.g. groups of formulas (i) and (ii); formulas (iii), and (iv); formulas (ii), and (iii); etc. Suitable organohydrogensiloxanes are commercially available from Dow Corning Corporation of Midland, Mich.

The cross-linker has at least two aliphatic unsaturated hydrocarbon groups. In various embodiments, the cross-linker is of formula (III): $R^5$—Y—$R^5$. $R^5$ is typically a monovalent unsaturated aliphatic hydrocarbon group having 2-12 carbon atoms. In various embodiments, $R^5$ is $CH_2$=CH—, $CH_2$=$CHCH_2$—, $CH_2$=$C(CH_3)CH_2$—, or CH≡C—, and similar substituted unsaturated groups such as $H_2C$=$C(CH_3)$—. Y is typically a divalent organic group, divalent siloxane group, or divalent organosiloxane group.

In certain embodiments, the cross-linker is an organic compound, or any mixture of compounds, containing at least two aliphatic unsaturated groups in its molecule. The cross-linker may be any diene, diyne or ene-yne compound. Diene, diyne or ene-yne compounds are those compounds (including polymeric compounds) wherein there are at least two aliphatic unsaturated groups with some separation between the groups within the molecule. Typically, the unsaturated groups are at the termini of the cross-linker, and/or pendant if part of a polymeric compound. Cross-linkers containing terminal and/or pendant unsaturated groups can be represented by formula (III) where each $R^5$ is as above, and Y can be a divalent organic or siloxane group or a combination of these. The cross-linker may be considered as being a/an "organic", "hydrocarbon", "organic polymer", "polyether" or "siloxane", or combinations thereof, depending on the selection of Y. Y may be a divalent hydrocarbon, siloxane, polyoxyalkylene, polyalkylene, polyisoalkylene, hydrocarbon-silicone copolymer, or mixtures thereof.

In one embodiment, the cross-linker is selected from an organic compound, herein denoted as ($B^1$), having the formula: $R^5$—$Y^1$—$R^5$; where $R^5$ is as above and $Y^1$ is a divalent hydrocarbon. $Y^1$ may contain 1-30 carbons, either as aliphatic or aromatic structures, and may be branched or un-branched. Alternatively, $Y^1$ may be an alkylene group containing 1-12 carbons. ($B^1$) may be selected from α,ω-unsaturated alkenes or alkynes containing 1-30 carbons, and mixtures thereof. ($B^1$) may be exemplified by, but not limited to, 1,4-pentadiene, 1,5-hexadiene, 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne. In specific embodiments, the cross-linker is a hexadiene, e.g. 1,5-hexadiene.

In another embodiment, the cross-linker is selected from a $R^5$—$Y^2$—$R^5$ compound where $Y^2$ is a siloxane, herein denoted as ($B^2$). $Y^2$ may be selected from any organopolysiloxane bonded to at least two organic groups having aliphatic unsaturation, designated as $R^5$, to form $R^5$—$Y^2$—$R^5$ structures. Thus, ($B^2$) can be any organopolysiloxane, and mixtures thereof, comprising at least two siloxane units generally represented by the average formula: $R^5R_m SiO_{(4-m)/2}$; where R is an organic group, $R^5$ is as above, and m is 0-3. The $R^5$ group may be present on any mono, di, or in siloxy unit in an organopolysiloxane molecule, for example; $(R^5R_2SiO_{1/2})$, $(R^5RSiO_{2/2})$, or $(R^5SiO_{3/2})$; as well as in combination with other siloxy units not containing an $R^5$ substituent, such as $(R_3SiO_{1/2})$, $(R_2SiO_{2/2})$, $(RSiO_{3/2})$, or $(SiO_{4/2})$ siloxy units where R is independently any organic group, a hydrocarbon containing 1-30 carbons, an alkyl group containing 1-30 carbons, or a methyl group; provided there are at least two $R^5$ substituents in the organopolysiloxane.

Representative, non-limiting, examples of ($B^2$) include: $(R_2R^5SiO_{1/2})(SiO_{4/2})_w(R_2R^5SiO_{1/2})$; $(R_2R^5SiO_{1/2})(SiO_{4/2})_w (R_2SiO_{2/2})_x(R_2R^5SiO_{1/2})$; $(R_2R^5SiO_{1/2})(R_2SiO_{2/2})_x (R_2R^5SiO_{1/2})$; $R_3SiO_{1/2})(R_2SiO_{2/2})_x(R^5RSiO_{2/2})_y(R_3 SiO_{1/2})$; $(R_3SiO_{1/2})(R_2SiO_{2/2})_x(R^5RSiO_{2/2})_y(RSiO_{3/2})_z (R_3SiO_{1/2})$; and $(R_3SiO_{1/2})(R_2SiO_{2/2})_x(R^5RSiO_{2/2})_y (SiO_{4/2})_w(R_3SiO_{1/2})$; where w≥0, x≥0, y≥2, z≥0, and R and $R^5$ are as above.

($B^2$) may be selected from vinyl functional polydimethylsiloxanes (e.g. vinyl siloxanes), such as those having the average formula: $CH_2$=$CH(Me)_2SiO[Me_2SiO_{2/2}]_x Si(Me)_2CH$=$CH_2$ or $Me_3SiO[(Me)_2SiO_{2/2}]_x[CH_2$=$CH (Me)SiO_{2/2}]_ySiMe_3$; where Me is methyl; x≥0, 0-200, or 10-100; and y≥0, 2-200, or 10-100. Vinyl siloxanes of this sort are commercially available from Dow Corning Corporation.

In another embodiment, the cross-linker is selected from a polyether compound, herein denoted as ($B^3$), having the formula: $R^5$—$Y^3$—$R^5$; where $R^5$ is as above. $Y^3$ is a polyoxyalkylene group having the formula: $(C_nH_{2n}O)_b$; where n is from 2-4; and b is >2, 2-100, or 2-50. The polyoxyalkylene group typically comprises oxyethylene units ($C_2H_4O$; "EO"), oxypropylene units ($C_3H_6O$; "PO"), oxytetramethylene or its isomer oxybutylene units ($C_4H_8O$; "BO"), or mixtures thereof. Thus, ($B^3$) may be selected from a polyoxyalkylene group having the formula: $R^5$—O[($C_2H_4O)_f (C_3H_6O)_g(C_4H_8O)_h]$—$R^5$; where f, g, and h may each independently range from 0-100, provided the sum of f+g+h is >2, 2-100, or 2-50. Alternatively, the polyoxyalkylene group comprises only oxyethylene units $(C_2H_4O)_f$, or only oxypropylene units $(C_3H_6O)_g$.

Representative, non-limiting examples of ($B^3$) include: $H_2C$=$CHCH_2O[C_3H_6O]_gCH_2CH$=$CH_2$; $H_2C$=$CHO [C_3H_6O]_gCH$=$CH_2$; $H_2C$=$C(CH_3)CH_2O[C_3H_6O]_gCH_2C (CH_3)$=$CH_2$; HC≡$CCH_2O[C_3H_6O]_gCH_2C$≡CH; HC≡CC $(CH_3)_2O[C_3H_6O]_gC(CH_3)_2C$≡CH; $H_2C$=$CHCH_2O [C_4H_8O]_hCH_2CH$=$CH_2$; $H_2C$=$CHO[C_4H_8O]_hCH$=$CH_2$; $H_2C$=$C(CH_3)CH_2O[C_4H_8O]_hCH_2C(CH_3)$=$CH_2$; and HC≡$CCH_2O[C_4H_8O]_hCH_2C$≡CH; and HC≡$CC(CH_3)_2O [C_4H_8O]_hC(CH_3)_2C$≡CH; where each of g and h is as above. The cross-linker may also be a mixture of various polyethers, i.e., a mixture of ($B^3$) components.

In another embodiment, the cross-linker is selected from a $R^5$—$Y^4$—$R^5$ compound, herein denoted as ($B^4$), where $R^5$ is as above and $Y^4$ is a polyalkylene group, generally selected from $C_2$-$C_6$ alkylene units or their isomers. One example is polyisobutylene group which is a polymer containing isobutylene unit. The molecular weight of the polyisobutylene group may vary, but typically ranges from 100-10,000 g/mole. Representative, non-limiting examples of ($B^4$) include those commercially available from BASF Corporation of Florham Park, N.J., under the trade name of OPPONOL® BV, such as OPPONOL® BV 5K, a diallyl terminated polyisobutylene having an average molecular weight of 5,000 g/mole.

In yet another embodiment, the cross-linker is selected from a $R^5$—$Y^5$—$R^5$ compound, herein denoted as ($B^5$), where $R^5$ is as above and $Y^5$ is a hydrocarbon-silicone copolymer group. $Y^5$ may have the formula: —$[R^5_u(R^2 SiO)_v]_q$—; where each of $R^5$ and R is as above; u and v are independently ≥1; alternatively u ranges from 1-20, and v ranges from 2-500 or 2-200; and q is >1, 2-500, or 2-100.

$R^5$—$Y^5$—$R^5$ compounds having a hydrocarbon-silicone copolymer group may be prepared via a hydrosilylation reaction between an α-ω unsaturated hydrocarbon, such as those described above as ($B^1$), and an organohydrogensiloxane. A representative, non-limiting example of such a reaction is shown below.

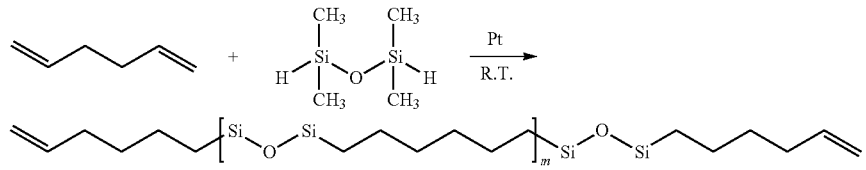

In another embodiment, the cross-linker is selected from poly(diene) compounds which contain vinyl or alkenyl side groups. The vinyl or alkenyl side groups are usually the reaction product of diene polymerization reaction and may be available for reaction with a Si—H compound. Polybutadiene is one such polymer and typically contains about 20 molar % of 1,2-vinyl side group. RICON® 130 is a commercially available liquid polybutadiene polymer with 20-35 molar % of 1,2-vinyl pendant groups, a viscosity of about 750 cps, and a molecular weight of 2500 g/mole. RICON® 130 is commercially available from Sartomer Company, Inc. of Exton, Pa.

The cross-linker may also be a mixture of any diene, diyne or ene-yne compound, such as any combination of ($B^1$), ($B^2$), ($B^3$), ($B^4$), and ($B^5$). Further examples of suitable cross-linkers are described in U.S. Pat. No. 8,273,840 to Lin, the disclosure of which is incorporated by reference.

The cross-linked composition is generally of the following general formula (II):

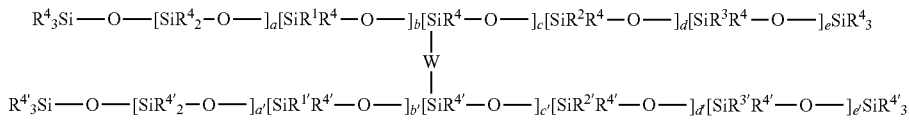

In formula (II), the upper and lower portions are attributable to the organohydrogensiloxane, specifically, to at least two molecules of the organohydrogensiloxane. The organohydrogensiloxane molecules can be the same or different. The middle portion or "W" is attributable to the cross-linker. The groups represented by subscripts a, a', b, b', c, c', d, d', e, and e', i.e., the groups in square brackets in formula (II), may be present in any order within the cross-linked composition, including a different order than that which is represented above and throughout this disclosure.

Moreover, these groups may be present in randomized or block form.

In formula (II), $R^{1'}$ can be the same as or different from $R^1$. $R^{2'}$ can be as the same or different from $R^2$. $R^{4'}$ can be the same as or different from $R^4$. Suitable groups for each of $R^{1'}$, $R^{2'}$, and $R^{4'}$, are as described above for $R^1$, $R^2$, and $R^4$, respectively. For example, each of $R^1$, $R^{1'}$, $R^2$, $R^{2'}$, $R^4$, and $R^{4'}$ is an independently selected substituted or unsubstituted hydrocarbyl group.

Typically, a≥0, a'≥0, b≥0, b'≥0, c≥1, c'≥1, d≥0, d'≥0, e≥1, and e'≥1. Each of a', b', c', d', and e', can be the same as or different from a, b, c, d, and e, respectively, with suitable integers and/or ranges for each group as described above.

$R^{3'}$ can be the same as or different from $R^3$. Typically, each of $R^3$ and $R^{3'}$ is independently a group having at least one carboxyl group or a precursor thereof. In various embodiments, each of $R^3$ and $R^{3'}$ is at least one carboxyl group or a precursor thereof, alternatively a derivative of ASA or trimethylsilyl undecylenate, and the cross-linked composition comprises the further reaction product of water, an alcohol, or a combination thereof. In specific embodiments, each of $R^3$ and $R^{3'}$ has a terminal carboxyl group or a terminal carboxyl group precursor. The terminal carboxyl group precursor is typically selected from an anhydride group or a capped carboxyl group. These embodiments and others are as described with the organohydrogensiloxane.

W is a divalent group. In various embodiments, W comprises an organic group, a siloxane group, or an organosiloxane group. In further embodiments, W comprises at least one of a hydrocarbylene, heterohydrocarbylene, or organoheterylene group. Specific examples of W include structure units (or moieties) attributable to use of the cross-linker.

The cross-linked composition generally has free carboxyl groups or free carboxyl group precursors (e.g. anhydride groups) as represented by $R^3$ and $R^{3'}$. Such groups can be useful for subsequent reaction(s) and/or can also interact with substrate surfaces, e.g. skin, leather, etc. It is thought that potential benefits provided by, or attributable to, such groups include, but are not limited to, film forming, substantivity, durability, pigment/particle suspension and/or modification, long lasting/wear, additional chemistry, actives (e.g. drug) or inactives (e.g. fragrance) delivery/release, hydrophilicity, reactivity, compatibility, polarity, and combinations thereof.

In certain embodiments, the cross-linked composition has a carboxyl equivalent of from 45-45,000, 450-9,000, or 450-4,500, g/mol, each generally based on a COOH group being ~45 grams/mol. For good handling property, the cross-linked composition can have a viscosity of from 10-1,000,000, 10-500,000, or 10-100,000, mm$^2$/sec.

Each of the organohydrogensiloxanes can be chemically (or physically) the same, such as two separate molecules of the same organohydrogensiloxane (or type). For example, the organohydrogensiloxane can be provided as in an "A-part" (or A-side) of a system for forming the cross-linked composition. Alternatively, organohydrogensiloxanes can be provided separately, especially when they are different from each other. This may be useful for formulation purposes. However, separation is not required.

The cross-linker can be provided separate from the organohydrogensiloxane(s), such as in a "B-part" (or B-side) of a system for forming the cross-linked composition. If the cross-linked composition includes one or more optional additives, the additive(s) can be included with either of, each of, or a combination of, the system parts. The system may include more than two parts. Optionally, various types of conventional additives can be utilized depending, for example, on the end use of the cross-linked composition. The present invention is not limited to any particular arrangement of the system, or to any particular additive or additives.

In certain embodiments, a non-functionalized resin (i.e., one lacking reactive functional groups) is utilized in the cross-linked composition. In these embodiments, the non-functionalized resin is trapped within the polymeric network during cure of the cross-linked composition. Such non-functionalized resins can be useful for providing chemical and/or physical modifications to the cross-linked composition.

In certain embodiments, the cross-linked composition can be formed with a supplemental cross-linker in addition (and/or alternate) to the cross-linker. Examples of suitable supplemental cross-linkers include polyols, polyamines, polyepoxides, and combinations thereof. Suitable supplemental cross-linkers, as well as other optional components that can be used to form, and/or be used in combination with, the cross-linked composition, are described in U.S. Pat. No. 5,444,139 to Valpey, III et al. and U.S. Pat. No. 8,026,330 to Kamei; and US Pub. No. 2012/0040931 to Kamei; which are incorporated by reference.

Method of Forming the Cross-Linked Composition

The method of forming the cross-linked composition comprises the steps of providing the organohydrogensiloxane and providing the cross-linker (each as described above). The method further comprises the step of combining the organohydrogensiloxane and the cross-linker. The reaction product is typically formed in the presence of a hydrosilylation catalyst.

Various types of hydrosilylation catalyst can be utilized. The hydrosilylation catalyst is typically selected from those based on precious metals, particularly Group VIII metals, including ruthenium, rhodium, palladium, osmium, iridium and platinum. Typically, the catalyst is a conventional platinum compound or complex. Suitable platinum compounds and complexes include chloroplatinic acid, platinum acetylacetonate, complexes of platinous halides with unsaturated compounds such as ethylene, propylene, organovinylsiloxanes, and styrene, hexamethyldiplatinum, $PtCl_2$, $PtCl_3$, $PtCl_4$, and $Pt(CN)_3$. In various embodiments, the catalyst is a form of chloroplatinic acid, either as the commonly available hexa-hydrate form or in its anhydrous form. Another useful catalyst is the cross-linked composition that is obtained when chloroplatinic acid is reacted with an aliphatically unsaturated organosilicon compound such as divinyltetramethyl-disiloxane. Additional suitable catalysts are described in U.S. Pat. No. 6,709,752 to James et al., which is incorporated by reference.

In embodiments where $R^3$ (and/or $R^{3'}$) is a hydrogen atom, the method can further comprise the steps of providing the compound and reacting $R^3$ (and/or $R^{3'}$) and the compound to further form the cross-linked composition. The compound can be reacted prior to, after, and/or contemporaneous with the cross-linker. The method can yet further comprise the steps of providing water, an alcohol, or a combination thereof, and reacting the cross-linked composition and the water, alcohol, or combination thereof, to further form the cross-linked composition. These and other embodiments are as described with the organohydrogensiloxane.

In embodiments where $R^3$ is at least one carboxyl group or a precursor thereof, alternatively a derivative of ASA or trimethylsilyl undecylenate, the method can further comprise the step of providing water, an alcohol, or a combination thereof, and reacting $R^3$ and the water, alcohol, or combination thereof to further form the cross-linked composition. These and other embodiments are as described with the organohydrogensiloxane.

In various embodiments, the cross-linked composition can be prepared by subjecting the organohydrogensiloxane and cross-linker to an addition reaction. The addition reaction may also be referred to as a hydrosilylation reaction. Reaction conditions for the addition reaction are not limited to any particular ones. In certain embodiments, the addition reaction is performed under reflux for 1-10 hours.

The addition reaction may be performed in the presence of the hydrosilylation catalyst. Other than those described above, further examples of suitable catalysts include, but are not limited to, chloroplatinic acid, chloroplatinic acid modified with an alcohol, and a complex of chloroplatinic acid with a vinylsiloxane. An amount of the catalyst to be used may be a catalytically effective amount, i.e., a catalytic amount, which is usually ≤50 ppm, particularly ≤20 ppm, as platinum metal or rhodium metal.

The addition reaction may be performed in a solvent as needed. Various types of conventional solvents can be utilized, such as silicone solvents and/or organic solvents. A specific example of a suitable silicone solvent is 3-octyl-heptamethyltrisiloxane. Examples of suitable organic solvents include, but are not limited to, isododecane; aromatic hydrocarbons, such as toluene and xylene; aliphatic or alicyclic hydrocarbons, such as n-pentane, n-hexane, and cyclohexane; and halogenated hydrocarbons, such as dichloromethane, chloroform, and carbon tetrachloride. To prevent undesirable side-reactions/reaction-products, the solvent should be inert with respect to the reactants/reaction-intermediates. For example, the solvent shouldn't have hydroxyl or amine functional groups. Additional examples of suitable solvents are described as "carrier fluids" in US Pub. No. 2010/0330011 to Kennan et al., which is incorporated by reference.

The organohydrogensiloxane and cross-linker can be reacted in various amounts to form the cross-linked composition. Based on the number hydrogen atoms provided by the organohydrogensiloxane, relative to the number of aliphatic unsaturated hydrocarbon groups provided by the cross-linker, the reactants can be utilized in a 1:1 stoichiometric ratio. For example, one hydrogen atom can be present for every one of the aliphatic unsaturated hydrocarbon groups present. Alternatively, the cross-linker can be utilized in a stoichiometric excess relative to the organohydrogensiloxane. Conversely, the organohydrogensiloxane can be utilized in a stoichiometric excess relative to the cross-linker. Such situations may also be referred to as over-indexing or under-indexing the reaction, with an index of 1.0 (or 100) indicating that there is a stoichiometric amount of hydrogen atoms to react with the amount of aliphatic unsaturated hydrocarbon groups present (1:1). The index may be from 0.25-2.0, 0.5-1.5, 0.9-1.1, 0.95-1.05, or 1.0, or any number in between. Higher or lower indexes may also be utilized. Various degrees of cross-linking can be present in the cross-linked composition based on the index utilized to form the cross-linked composition and the number of c groups, from various degrees of partial cross-linking to full cross-linking. If present in the cross-linked composition, the present invention is not limited to any particular subsequent reaction or use of free functional groups, e.g. carboxyl groups.

Cosmetic Composition

The cosmetic composition of this disclosure may also be referred to as a personal care composition or personal care product. The personal care composition includes the cross-linked composition described above. The personal care composition may be in the form of a cream, a gel, a powder, a paste, or a freely pourable liquid. Generally, such personal care compositions can generally be prepared at room temperature if no solid materials at room temperature are present in the personal care compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition can be used in or for a variety of personal, household, and health care applications. In particular, the cross-linked composition and/or personal care composition of the present disclosure may be used in the personal care products as described in U.S. Pat. Nos. 6,051,216, 5,919,441, 5,981,680; WO2004/060271 and WO2004/060101; in sunscreen compositions as described in WO2004/060276; in cosmetic compositions also containing film-forming resins, as described in WO03/105801; in the cosmetic compositions as described in US Pub. Nos. 2003/0235553, 2003/0072730 and 2003/0170188, in EP Pat. Nos. 1,266,647, 1,266,648, and 1,266,653, in WO03/105789, WO2004/000247 and WO03/106614; as additional agents to those described in WO2004/054523; in long wearing cosmetic compositions as described in US Pub. No. 2004/0180032; and/or in transparent or translucent care and/or make up compositions as described in WO2004/054524; all of which are expressly incorporated herein by reference in various non-limiting embodiments.

The personal care products may be functional with respect to the portion of the body to which they are applied, cosmetic, therapeutic, or some combination thereof. Conventional examples of such personal care products include, but are not limited to: antiperspirants and deodorants; skin care creams, skin care lotions, moisturizers, and facial treatments, such as acne or wrinkle removers; personal and facial cleansers; bath oils; perfumes and colognes; sachets; sunscreens; pre-shave and after-shave lotions; shaving soaps, and shaving lathers; hair shampoos, hair conditioners, hair colorants, hair relaxants, hair sprays, mousses, gels, permanents, depilatories, and cuticle coats; make-ups, color cosmetics, foundations, concealers, blushes, lipsticks, eyeliners, mascara, oil removers, color cosmetic removers, and powders; and medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

Personal care compositions for personal care may alternatively be referred to as cosmetic compositions and include those that are intended to be placed in contact with external portions of the human body (skin, hair, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or modifying odors. In some instances, personal care compositions also include health care compositions. Cosmetic applications, and in some instances health care applications, include skin care, sun care, hair care, or nail care applications.

Personal care ingredients are those components used in personal care or cosmetic applications. A wide review of such components may be found in the CTFA cosmetic component handbook. Exemplary personal care ingredients are described in further detail below. These personal care ingredients may alternative be referred to as cosmetic components, health care components, etc. depending on the typical use thereof. When the personal care ingredient is the cosmetic component, the personal care composition is referred to as a cosmetic composition; when the personal care ingredient is the health care component, the personal care composition is referred to as a health care composition, etc.

Cosmetic components include emollients, waxes, moisturizers, surface active materials (such as surfactants or detergents or emulsifiers), thickeners, water phase stabilizing agents, pH controlling agents, preservatives and cosmetic biocides, sebum absorbants or sebum control agents, vegetable or botanical extracts, vitamins, proteins or amino-acids and their derivatives, pigments, colorants, fillers, silicone conditioning agents, cationic conditioning agents, hydrophobic conditioning agents, UV absorbers, sunscreen agents, antidandruff agents, antiperspirant agents, deodorant agents, skin protectants, hair dyes, nail care components, fragrances or perfume, antioxidants, oxidizing agents, reducing agents, propellant gases, and mixtures thereof. Additional components that may be used in the cosmetic compositions include fatty alcohols, color care additives, anticellulites, pearlising agents, chelating agents, film formers, styling agents, ceramides, suspending agents and others.

Health care components include antiacne agents, antibacterial agents, antifungal agents, therapeutic active agents, external analgesics, skin bleaching agents, anti-cancer agents, diuretics, agents for treating gastric and duodenal ulcers, proteolytic enzymes, antihistamine or H1 histamine blockers, sedatives, bronchodilators, diluents, and others. Additional components that may be used in the health care compositions include antibiotics, antiseptics, antibacterial agents, anti-inflammatory agents, astringents, hormones, smoking cessation compositions, cardiovascular agents, antiarrhythmic agents, alpha-I blockers, beta blockers, ACE inhibitors, antiaggregants, non-steroidal anti-inflammatory agents (NSAIDs; such as diclofenac), antipsoriasis agents (such as clobetasol propionate), antidermatitis agents, tranquilizer, anticonvulsants, anticoagulant agents, healing factors, cell growth nutrients, peptides, corticosteroidal drugs, antipruritic agents and others.

Cosmetic components may be used in health care compositions, such as waxes, and others; and health care components may be used in cosmetic compositions, such as anti-acne agents, and others.

Examples of emollients include volatile or non-volatile silicone oils; silicone resins, such as polypropylsilsesquioxane and phenyl trimethicone; silicone elastomers, such as dimethicone cross-polymers; alkylmethylsiloxanes, such as $C_{30}$-$C_{45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils, such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheat germ, sunflower, grapeseed, castor, shea, avocado, olive, soybean, sweet almond, palm, rapeseed, cotton seed, hazelnut, macadamia, jojoba, blackcurrant, evening primrose; triglycerides of caprylic/capric acids; higher fatty acids, such as oleic acid, linoleic acid or linolenic acid; and mixtures thereof.

Examples of waxes include hydrocarbon waxes, such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30}$-$C_{45}$ alkyldimethylsilyl polypropylsilsesquioxane), and mixtures thereof Examples of moisturizers include lower molecular weight aliphatic diols, such as propylene glycol and butylene glycol; polyols, such as glycerine and sorbitol; and polyoxyethylene polymers, such as polyethylene glycol 200; hyaluronic acid and its derivative; and mixtures thereof.

Examples of surface active materials may be anionic, cationic or nonionic, and include organomodified silicones, such as dimethicone copolyol; oxyethylenated and/or oxypropylenated ethers of glycerol; oxyethylenated and/or oxypropylenated ethers of fatty alcohols, such as ceteareth-30, $C_{12}$-$C_{15}$ pareth-7; fatty acid esters of polyethylene glycol, such as PEG-50 stearate and PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates, such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof.

Further examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Nonionic surfactants include dimethicone copolyols, fatty acid esters of polyols, for instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, sodium alginate, arabic gum, *cassia* gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols (such as ethyl alcohol), hydrocolloids, and mixtures thereof.

Examples of pH controlling agents include any water soluble acid, such as a carboxylic acid or a mineral acid, such as hydrochloric acid, sulphuric acid, and phosphoric acid, monocarboxylic acid, such as acetic acid and lactic acid, and polycarboxylic acids, such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives, such as zinc pyrithione, and mixtures thereof.

Examples of sebum absorbants or sebum control agents include silica silylate, silica dimethyl silylate, dimethicone/vinyl dimethicone cross-polymer, polymethyl methacrylate, cross-linked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, *ginkgo biloba*, sunflower, wheat germ, seaweed, olive, grape, pomegranate, aloe, apricot kernel, apricot, carrot, tomato, tobacco, bean, potato, actzuki bean, *catechu*, orange, cucumber, avocado, watermelon, banana, lemon, palm, or mixtures thereof. Examples of herbal extracts include dill, horseradish, oats, neem, beet, broccoli, tea, pumpkin, soybean, barley, walnut, flax, *ginseng*, poppy, avocado, pea, sesame, and mixtures thereof.

Examples of vitamins include a variety of different organic compounds, such as alcohols, acids, sterols, and quinones. They may be classified into two solubility groups: lipid-soluble vitamins and water-soluble vitamins. Lipid-soluble vitamins that have utility in personal care compositions include retinol (vitamin A), ergocalciferol (vitamin D2), cholecalciferol (vitamin D3), phytonadione (vitamin K1), and tocopherol (vitamin E). Water-soluble vitamins that have utility in personal care compositions include ascorbic acid (vitamin C), thiamin (vitamin B1), niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins, such as retinyl palmitate (vitamin A palmitate), retinyl acetate (vitamin A acetate), retinyl linoleate (vitamin A linoleate), retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolyzed form and they may also be quaternized, such as hydrolyzed elastin, hydrolyzed wheat powder, hydrolyzed silk. Examples of protein include enzymes, such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be cross-linked, copolymer microspheres, polytrap, silicone resin microbeads, and mixtures thereof. The fillers may be surface treated to modify affinity or compatibility with remaining components.

Examples of silicone conditioning agents include silicone oils, such as dimethicone; silicone gums, such as dimethiconol; silicone resins, such as trimethylsiloxy silicate, and polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone cross-polymer, and silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives, such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants, such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of antidandruff agents include pyridinethione salts, selenium compounds, such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminum acetate, aluminum hydroxide, aluminum sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hyd oxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; Haematoxylon brasiletto wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; *Isatis tinctoria* leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; and 1,2,4-trihydroxybenzene.

Examples of nail care components include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; *Cetraria islandica* extract; *Chondrus crispus*; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume components are described in detail in standard textbook references, such as Perfume and Flavour Chemicals, 1969, S. Arctander, Montclair, N.J.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of propellant gases include carbon dioxide, nitrogen, nitrous oxide, volatile hydrocarbons, such as butane, isobutane, or propane, and chlorinated or fluorinated hydrocarbons, such as dichlorodifluoromethane and dichlorotetrafluoroethane or dimethylether; and mixtures thereof.

Examples of antiacne agents include salicylic acid, sulfur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of therapeutic active agents include penicillins, cephalosporins, tetracyclines, macrolides, epinephrine, amphetamines, aspirin, acetominophen, barbiturates, catecholamines, benzodiazepine, thiopental, codeine, morphine, procaine, lidocaine, benzocaine, sulphonamides, ticonazole, perbuterol, furosamide, prazosin, hormones, prostaglandins, carbenicillin, salbutamol, haloperidol, suramin, indomethicane, diclofenac, glafenine, dipyridamole, theophylline, hydrocortisone, steroids, scopolamine, and mixtures thereof.

Examples of external analgesics are benzyl alcohol, *capsicum* oleoresin (*Capsicum frutescens* oleoresin), methyl salicylate, camphor, phenol, capsaicin, juniper tar (*Juniperus oxycedrus* tar), phenolate sodium (sodium phenoxide), *capsicum* (*Capsicum frutescens*), menthol, resorcinol, methyl nicotinate, turpentine oil (turpentine), and mixtures thereof. An example of a skin bleaching agent is hydroquinone.

Examples of anti-cancer agents include alkylating agents (such as busulfan, fluorodopan), antimitotic agents (such as colchicine, rhizoxin), topoisomerase I inhibitors (such as camptothecin and its derivatives), topoisomerase II inhibitors (such as menogaril, amonafide), RNA/DNA or DNA anti-metabolites (such as acivicin, guuanazole), plant alkaloids and terpenoids, antineoplastics, some plant-derived compounds (such as podophyllotoxin, *vinca* alkaloids), and mixtures thereof.

Examples of diuretics include loop diuretics (such as bumetanide, furosemide), thiazide diuretics (such as chlorothiazide, hydroflumethiazide), potassium-sparing diuretics (such as amioloride, spironolactone), carbonic anhydrase inhibitors (such as acetazolamide), osmotic diuretics (such as mannitol), and mixtures thereof. Examples of agents for treating gastric and duodenal ulcers include proton pump inhibitor (such as lansoprazole, omeprazole), acid blockers or H2 histamine blockers (such as cimetidine, ranitidine), bismuth, sucralfate, and mixtures thereof. Examples of proteolytic enzymes include nattokinase, serratiopeptidase, bromelain, papain, and mixtures thereof. Examples of antihistamine or H1 histamine blockers include brompheniramine, clemastine, cetirizine, loratadine, fexofenadine, and mixtures thereof.

Examples of sedatives include barbiturates (such as phenobarbitol), benzodiazepines (such as lorazepam), herbal sedatives, benzodiazepine-like drugs (such as zolpidem, zopiclone), and mixtures thereof. Examples of bronchodilators include short-acting $\beta$2-agonists and long-acting $\beta$2-agonists, anticholinergics, and mixtures thereof.

Examples of diluents include silicon containing diluents, such as hexamethyldisiloxane, octamethyltrisiloxane, and other short chain linear siloxanes, such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes, such as hexamethylcyclotrisiloxane, octamethylcyclotetrasiloxane, decamethylcyclopentasiloxane, dodecamethylcyclohexasiloxane; organic diluents, such as butyl acetate, alkanes, alcohols, ketones, esters, ethers, glycols, glycol ethers, and hydrofluorocarbons. Hydrocarbons include isododecane, isohexadecane, Isopar L ($C_{11}$-$C_{13}$), Isopar H ($C_{11}$-$C_{12}$), and hydrogentated polydecene. Ethers and esters include isodecyl neopentanoate, neopentylglycol heptanoate, glycol distearate, dicaprylyl carbonate, diethylhexyl carbonate, propylene glycol n-butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols.

The personal care composition may also include film formers. The term "film-forming polymer" means a polymer capable, by itself or in the presence of an auxiliary film-forming agent, of forming a macroscopically continuous film on a support, especially on keratin materials, preferably a cohesive film and better still a film whose cohesion and mechanical properties are such that the said film can be isolated from the said support".

Examples of film formers include those polymers capable, by themselves or in the presence of an auxiliary film-forming agent, of forming a macroscopically continuous film on a support, especially on keratin materials, preferably a cohesive film and better still a film whose cohesion and mechanical properties are such that the said film can be isolated from the said support. Examples of film formers include silicone resins, gums, silicone acrylates, sugar siloxanes, and others. The film former can be delivered from either an oil media, aqueous media or in an emulsion form.

The personal care composition and/or the cross-linked composition may also include one or more components as described in PCT/US15/024905 and PCT/US15/024886, which are incorporated by reference.

Skin care compositions include shower gels; soaps; hydrogels; creams; lotions and balms; antiperspirants and deodorants, such as sticks, soft solid, roll on, aerosol, and pump sprays; skin creams; skin care lotions; moisturizers; facial treatments, such as wrinkle control or diminishment treatments; exfoliates; body and facial cleansers; bath oils; perfumes; colognes; sachets; sunscreens; mousses; patches; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof.

Hair care compositions include shampoos, rinse-off conditioners, leave-in conditioners and styling aids, gels, sprays, pomades, mousses, waxes, hair colorants, hair relaxants, hair straighteners, permanents, and kits thereof.

Nail care compositions include color coats, base coats, cuticle coats, nail hardeners, and kits thereof.

Health care compositions may be in the form of ointments, creams, gels, mousses, pastes, patches, spray on bandages, foams and/or aerosols or the like, medicament creams, pastes or sprays including anti-acne, dental hygienic, antibiotic, healing promotive, which may be preventative and/or therapeutic medicaments, and kits thereof.

The personal care compositions may be used by standard methods, such as applying them to the human or animal body, e.g. skin or hair, using applicators, brushes, applying by hand, pouring them and/or optionally rubbing or massaging the composition onto or into the body.

The personal care compositions can be applied topically to the desired area of the skin or hair in an amount sufficient to provide a satisfactory cleansing or conditioning of the skin or hair. The personal care compositions may be diluted with water prior to, during, or after topical application, and then subsequently rinsed or wiped off of the applied surface, for example rinsed off of the applied surface using water or a water-insoluble substrate in combination with water.

The personal care compositions may be used on hair in a conventional manner. An effective amount of the composition for washing or conditioning hair is applied to the hair, with the effective amount typically ranging from about 1-50 grams. Application to the hair typically includes working the personal care composition through the hair such that most or all of the hair is contacted with the personal care composition. These steps can be repeated as many times as desired to achieve the desired benefit.

Benefits obtained from using the personal care compositions on hair include one or more of the following benefits: color retention, improvement in coloration process, hair conditioning, softness, detangling ease, silicone deposition, anti-static, anti-frizz, lubricity, shine, strengthening, viscosity, tactile, wet combing, dry combing, straightening, heat protection, styling, and curl retention.

The personal care compositions may be used on skin in a conventional manner. An effective amount of the personal care composition for the purpose is applied to the skin, with the effective amount typically ranging from about 1-3 mg/cm$^2$. Application to the skin typically includes working the personal care composition into the skin as many times as desired to achieve the desired benefit.

Benefits obtained from using the personal care compositions on skin include one or more of the following benefits: stability in various formulations (o/w, w/o, anhydrous), utility as an emulsifier, level of hydrophobicity, organic compatibility, substantivity/durability, wash off resistance, interactions with sebum, performance with pigments, pH stability, skin softness, suppleness, moisturization, skin feel, long lasting, long wear, long lasting color uniformity, color enhancement, foam generation, optical effects (soft focus), and stabilization of actives.

The personal care composition may be used to care for keratinous substrates, to cleanse, to condition, to refresh, to make up, to remove make up, or to fix hair. A method of treating keratinous substrates, such as hair or skin, includes applying to it a cosmetic composition according to this disclosure.

A cosmetically acceptable medium is meant to designate a medium particularly suitable for apply a composition of the invention on keratin materials. The cosmetically acceptable medium is generally adapted to the nature of the support on which the cosmetic composition should be applied as well as to the aspect under which the cosmetic composition should be conditioned and includes water, solvents, diluents, or mixtures and emulsions thereof. When utilized, the cosmetically acceptable medium can be present in an amount ranging from about 0.1-99.9 wt. % based upon the total weight of the cosmetic composition.

The amount of the cross-linked composition in the cosmetic compositions described above may vary from about 0.1-95, 0.2-50, or 0.5-25, wt. % based on 100 parts by weight of the cosmetic composition. The cosmetic component is generally present in an amount of from about 0.01-99.99 wt. % based on 100 parts by weight of the cosmetic composition. Combinations of different cosmetic components may be utilized. It is contemplated that any and all values or ranges of values between those described above may also be utilized.

Method of Forming the Cosmetic Composition

This disclosure also provides a method of forming the cosmetic composition. The method includes combining a personal care product or any other similar compound, as described above, with the cross-linked composition. It is contemplated that the personal care product may be present before, during, and/or after reaction of the organohydrogensiloxane and the cross-linker. In one embodiment, the cross-linked composition is prepared individually and then combined later with the personal care composition ingredients. It is possible to include some personal care ingredients at a fluid reaction step (i.e., formation of the hydrosilylation reaction product) but various factors may need to be controlled, such as reaction inhibition, temperature sensitivity of the ingredients, etc. Techniques known in the art for formation of personal care formulations, including but not limited to, mixing techniques, cold blends or application of heat to facilitate forming the personal care composition, can be used. The order of addition used herein can be any known in the art.

The cosmetic composition may be prepared by a process comprising the steps of mixing the cross-linked composition and at least one cosmetic component optionally in the presence of a cosmetically acceptable medium. The cosmetic compositions may be prepared by mixing the cross-linked composition in the aqueous phase with the appropriate phase components or in the oil phase with the appropriate phase components, and optionally provide for a second phase, and mix both phases together, optionally under heating.

The process may be conducted at temperatures ranging of from 15-90° C., 20-60° C., or at room temperature (~25° C.), using simple propeller mixers, counter-rotating mixers, or homogenizing mixers. No special equipment or processing conditions are typically required. Depending on the type of cosmetic composition prepared, the method of preparation will be different, but such methods are well known in the art.

The following examples, illustrating the embodiments of this disclosure, are intended to illustrate and not to limit the invention.

Various examples of functionalized organohydrogensiloxanes are prepared via an addition reaction scheme. These examples are described in Examples 1 through 3 below.

Example 1: Allyl Succinic Anhydride (ASA) Organohydrogensiloxane

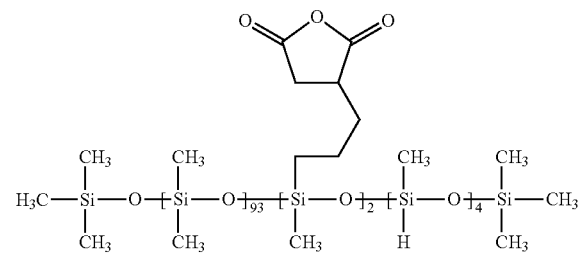

To a 1,000 mL three neck round bottom flask equipped with glass stir rod, Teflon® moon shaped paddle, stir bearing, temperature probe, heating mantle, and nitrogen sweep, is placed 468.42 g of trimethylsilyl endblocked, dimethyl, methylhydrogen siloxane ($MD_{93}D^H_6M$), 21.22 g of ASA ($C_7H_8O_3$), and 55 g of isododecane (IDD; solvent). As understood in the silicone art, "M" is generally a ($RSiO_{1/2}$) siloxy unit and "D" is generally a ($R_2SiO_{2/2}$) siloxy unit. The contents are heated to 70° C. and catalyzed with 7 ppm platinum IV. The reaction exotherms and the flask is held at 80° C. for two hours. The contents are then devolatilized at 135° C. and 4 mm Hg for two hours to remove the IDD and volatiles.

Example 2: ASA Organohydrogensiloxane with 1-Hexene

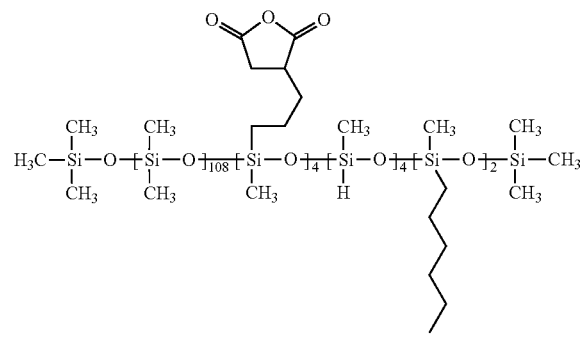

To a 500 mL three neck round bottom flask equipped with glass stir rod, Teflon® moon shaped paddle, stir bearing, temperature probe, heating mantle, and nitrogen sweep, is placed 456.28 g of trimethylsilyl endblocked, dimethyl, methylhydrogen siloxane ($MD_{108}D^H_{10}M$), 34.97 g of ASA, and 55 g of IDD. The contents are heated to 70° C. and catalyzed with 7 ppm platinum IV. The reaction exotherms and the flask is held at 80° C. for two hours. After two hours, the flask is cooled to 55° C. and 10 g of 1-hexene is added followed by 3 ppm platinum IV. The flask is then held at 60° C. for two hours. The contents are then devolatilized at 135° C. and 4 mm Hg for two hours to remove the IDD and volatiles.

Example 3: ASA Organohydrogensiloxane with 1-Hexadecene

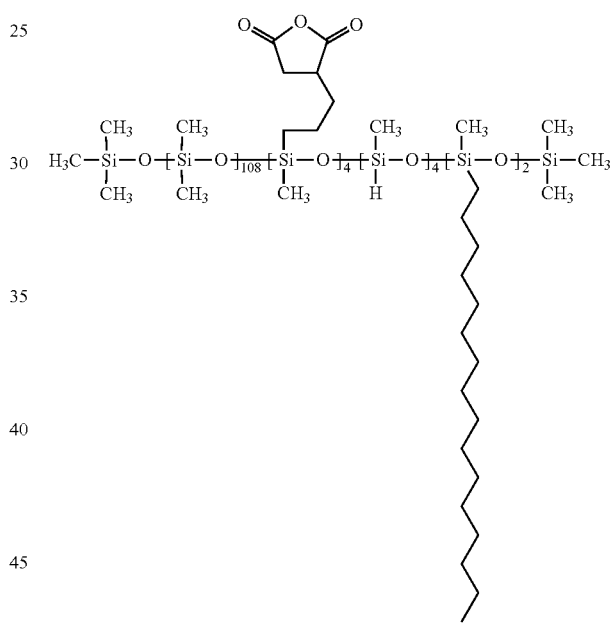

To a 500 mL three neck round bottom flask equipped with glass stir rod, Teflon® moon shaped paddle, stir bearing, temperature probe, heating mantle, and nitrogen sweep, is placed 443.29 g of trimethylsilyl endblocked, dimethyl, methylhydrogen siloxane ($MD_{108}D^H_{10}M$), 33.97 g of ASA, and 55 g of IDD. The contents are heated to 70° C. and catalyzed with 7 ppm platinum IV. The reaction exotherms and the flask is held at 80° C. for two hours. After two hours, 22.74 g of 1-hexadecene is added to the flask followed by 3 ppm platinum IV. The flask is then held at 80° C. for two hours. The contents are then devolatilized at 135° C. and 4 mm Hg for two hours to remove the IDD and volatiles.

Various examples of the cross-linked composition are prepared via an addition reaction scheme. These examples are described in Examples 4 through 7 below.

Example 4: ASA Elastomer Blend

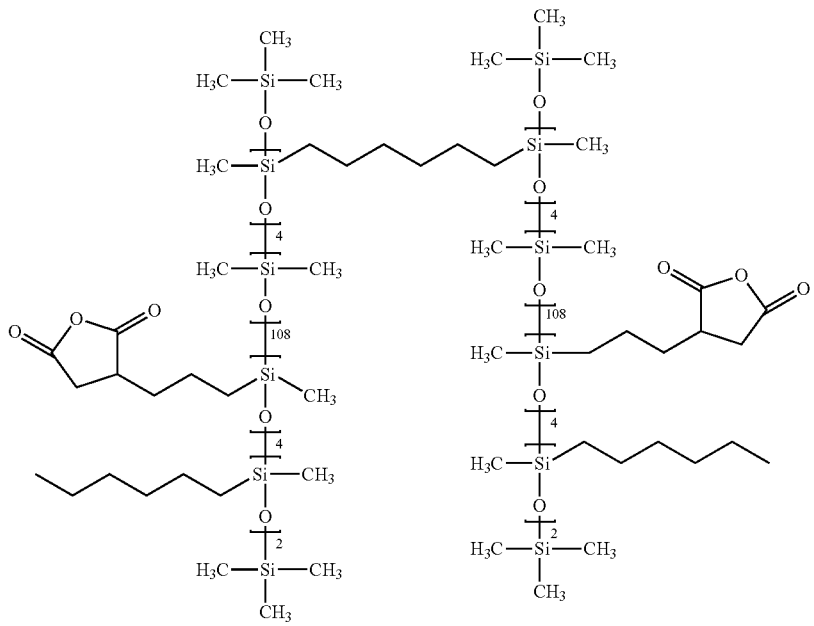

A 1,000 mL ESCO mixer having a high shear cowles blade and a scraper blade is charged with 61.65 g of ASA organohydrogensiloxane with 1-hexene (from Example 2) and 287 g of IDD. The mixer is heated to 70° C. Once at 70° C., 1.95 mL of 1,5-hexadiene and 0.67 g of 1,3-diethenyl-1,1,3,3-tetramethyldisiloxane complexes with platinum (0.5%) are added simultaneously to the mixer. The contents gelled after 10 minutes. The contents are then sheared for three hours at 70° C. The mixer is then cooled to below 50° C. and the contents are decanted.

Example 5: ASA Elastomer Blend, Ring-Opened

A 1,000 mL ESCO mixer having a high shear cowles blade and a scraper blade is charged with 61.65 g of ASA organohydrogensiloxane with 1-hexene (from Example 2) and 287 g of IDD. The mixer is heated to 70° C. Once at 70° C., 1.95 mL of 1,5-hexadiene and 0.67 g of 1,3-diethenyl-1,1,3,3-tetramethyldisiloxane complexes with platinum (0.5%) are added simultaneously to the mixer. The contents gelled after 10 minutes. The contents are then sheared for three hours at 70° C. Next, 10.5 g of water are added to the mixer and sheared for an additional hour. The mixer is then cooled to below 50° C. and the contents are decanted.

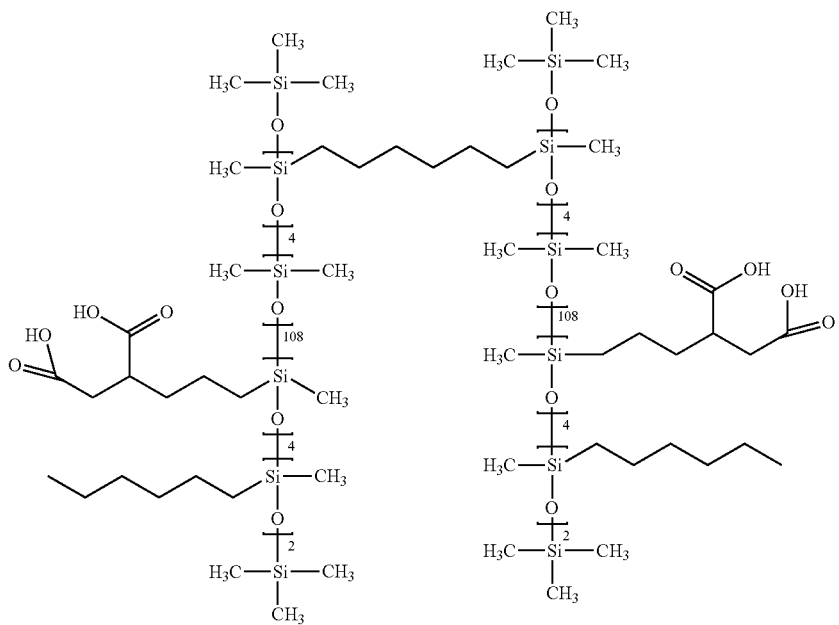

Example 6: Trimethylsilyl Undecylenate Elastomer Blend

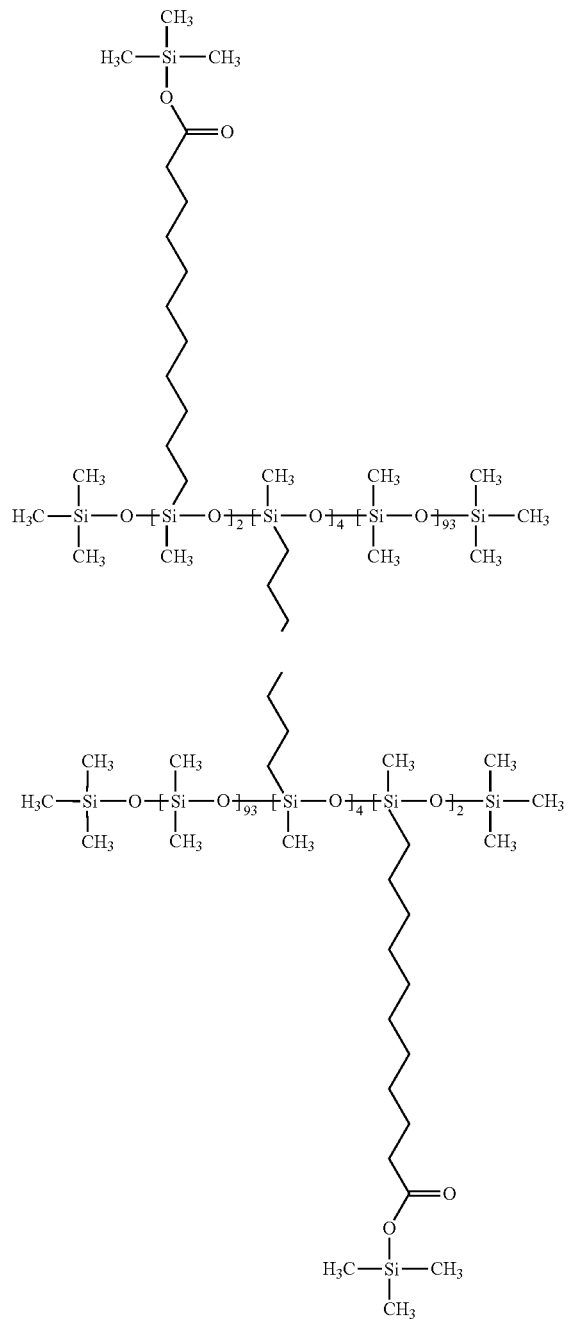

A 1,000 mL ESCO mixer having a high shear cowles blade and a scraper blade is charged with 68.55 g of trimethylsilyl endblocked, dimethyl, methylhydrogen siloxane ($MD_{93}D^H{}_6M$), 4.75 g of trimethylsilyl undecylenate, and 280 g of IDD. The contents are heated to 70° C. Once at 70° C., 0.4 g of 1,3-diethenyl-1,1,3,3-tetramethyldisiloxane complexes with platinum (0.5%) and 2.16 mL of 1,5-hexadiene are added simultaneously to the mixer. The contents gelled after 19 minutes. The contents are then sheared for an additional three hours at 70° C.

Example 7: Trimethylsilyl Undecylenate Elastomer Blend, De-Blocked

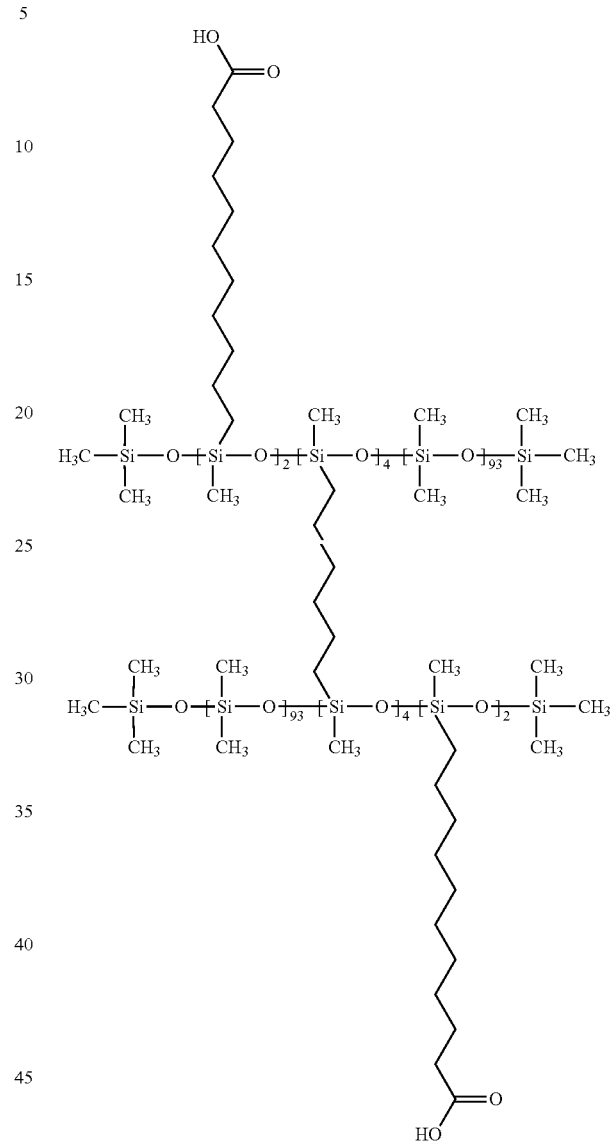

A 1,000 mL ESCO mixer having a high shear cowls blade and a scraper blade is charged with 68.55 g of trimethylsilyl endblocked, dimethyl, methylhydrogen siloxane ($MD_{93}D^H{}_6M$), 4.75 g of trimethylsilyl undecylenate, and 280 g of IDD. The contents are heated to 70° C. Once at 70° C., 0.4 g of 1,3-diethenyl-1,1,3,3-tetramethyldisiloxane complexes with platinum (0.5%) and 2.16 mL of 1,5-hexadiene are added simultaneously to the mixer. The contents gelled after 19 minutes. The contents are then sheared for an additional three hours at 70° C. After three hours, the mixer is cooled to 60° C. Once at 60° C., 10.5 g of ethanol is added to the mixer and the contents are sheared for one hour.

An additional example of the cross-linked composition (or "elastomer") of this disclosure is described immediately below. All percentages are in wt. %. All measurements were conducted at 23° C. unless indicated otherwise.

Preparation of Si—H Intermediate 165.41 g of $Me_3SiO(Me_2SiO)_w(MeHSiO)_ySiMe_3$, 22.1 g of ASA and 50.0 g of IDD were added to a 500 mL three neck round bottom flask equipped with a condenser, a stirrer, a temperature probe, and a nitrogen purge. The components were then heated to 80° C. and a platinum catalyst was added. The components were held for one hour, wherein 12.58 g of decene and more platinum catalyst was added. The components were held for one hour. Finally, the resultant material was devolatilized at 125° C. under a full vacuum for 2 hours. The resultant material was cooled and decanted to form the Si—H intermediate, with $R^1$ being anhydride and $R^2$ being alkene:

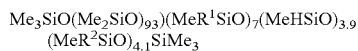
$Me_3SiO(Me_2SiO)_{93}(MeR^1SiO)_7(MeHSiO)_{3.9}$
$(MeR^2SiO)_{4.1}SiMe_3$ Preparation of Elastomer Gel 19.62 g of the Si—H intermediate above and 80.01 g of IDD were added to a reaction flask. The components were heated to 80° C., wherein 1,5-hexadiene and platinum catalyst were added to the reaction flask. Once gelled, the resultant material was held at 80° C. for 3 hours. The material was sheared and then decanted to form an elastomer gel.

Preparation of COOH-Elastomer

The elastomer gels, as made in preparation of the elastomer above, were made into gel pastes using a high shear mixing. The shear steps included the addition of additional carrier fluid (solvent) and organovinylsiloxane. The materials were sheared in a Waring Commercial Laboratory Blender. In shear step 1, the gel was sheared for 20 seconds at setting 1, then 20 seconds at setting 3, then 20 seconds at setting 5. Solvent and organovinylsiloxane were added followed by shearing for 30 seconds at each of the following settings: 1, 2, 3, 3. Between each setting, the material was scraped from the sides of the mixer cup using a spatula.

The resultant elastomer, hereinafter referred to as the COOH-Elastomer, was then introduced to various cosmetic formulations, with formulations and procedures for forming the particular cosmetic compositions provided below.

| Formulation 1: Anhydrous gel with high level of glycerin and Vitamin C | |
|---|---|
| Phase A | |
| PEG/PPG-19/19 Dimethicone (and) $C_{13}$-$C_{16}$ Isoparaffin (and) $C_{10}$-$C_{13}$ Isoparaffin | 4.0 |
| Caprylyl Methicone | 5.0 |
| COOH-Elastomer | 15.0 |
| Phase B | |
| L-ascorbic Acid | 10.0 |
| Glycerin | 66.0 |
| Procedure: Mix Phase A; heat glycerin to high temperature and add L-ascorbic acid to it under mixing until clear solution; drop Phase B into Phase A slowly; and mix final gel. | |

The particularity of this gel was that it allows the incorporation of a high level of Vitamin C using glycerin as a carrier, therefore to ensure the stability of the active without the drawback of the glycerin feel.

The silicone polyether (PEG/PPG-19/19 Dimethicone) can be either omitted or replaced by similar type of material such as grafted-block or block copolymers comprising at least one block of polyorganosiloxane type and at least one block of a polyether. The polyorganopolysiloxane block may especially be a polydimethylsiloxane or a poly ($C_2$-$C_8$) alkylmethylsiloxane; the polyether block may be a poly(oxy ($C_2$-$C_8$)alkylene, in particular polyoxyethylene and/or polyoxypropylene. These can also be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible. Another type of silicone polyether composition that may be included in the present composition is an ABn polyalkylene oxide silicone copolymers as described in EP Pat. No. 492657.

| Formulation 2.1: Antiperspirant gel | |
|---|---|
| Phase A | |
| Cyclopentasiloxane (and) PEG-12 Dimethicone Cross-polymer | 10.0 |
| Cyclopentasiloxane | 10.0 |
| COOH-Elastomer | 10.0 |
| Phase B | |
| Aluminum Chloride | 25.0 |
| Propylene Glycol | 7.0 |
| Water | 38.0 |
| Procedure: Mix phase A; dissolve aluminum chloride in mixture of water and propylene glycol under mixing; drop phase B into Phase A slowly; and mix final gel. | |

| Formulation 2.2: Antiperspirant soft solid | |
|---|---|
| Phase A | |
| COOH-Elastomer | 33.0 |
| Phase B | |
| Aluminum Chloride | 11.0 |
| Water | 22.0 |
| Phase C | |
| Glycerin | 34.0 |
| Procedure: Dissolve aluminum chloride in water; mix Phases B and A; and add Phase C to Phase (A + B) and mix until soft solid. | |

Other antiperspirant/deodorant actives could be used including, but not limited to, those described above. The silicone polyether (PEG-12 Dimethicone cross polymer) can be either omitted or replaced by similar type of material such as grafted-block or block copolymers comprising at least one block of polyorganosiloxane type and at least one block of a polyether (with suitable types described in Formulation 1).

| Formulation 3: Shower gel | |
|---|---|
| Phase A | |
| Hydroxy Ethyl Cellulose (HEC) | 0.4 |
| Water | 31.3 |
| Phase B | |
| Stearic Acid | 1.6 |
| Myristic Acid | 4.0 |
| Palmitic Acid | 3.2 |
| Sodium Laureth Sulfate (and) Glycol Distearate (and) Cocamide MEA (and) Laureth-10 | 2.4 |
| COOH-Elastomer | 4.0 |

Formulation 3: Shower gel -continued

Phase C

| | |
|---|---|
| Water | 39.6 |
| Potassium Hydroxide | 6.0 |

Phase D

| | |
|---|---|
| Sodium Laureth Sulfate (and) Glycol Distearate (and) Cocamide MEA (and) Laureth-10 | 4.0 |
| Propylene Glycol | 1.6 |
| Glycerin | 1.6 |

Phase E

| | |
|---|---|
| Citric Acid | 0.2 |
| Propylene Glycol (and) Diazolidinyl Urea (and) Methylparaben (and) Propylparaben | 0.4 |

Procedure: Heat water to 80° C.; disperse HEC into water slowly under mixing; mix Phase B and keep temperature at 80° C.; add Phase A to Phase B; dissolve potassium hydroxide into water and heat solution to 80° C.; add Phase B to Phase C under mixing and keep temperature at 80° C.; add Phase D to Phase (A + B + C) and keep mixing until temperature is down to 45° C.; and add Phase E to Phase (A + B + C + D).

Alternative anionic surfactants can be used such as $C_6$-$C_{30}$ fatty acid salts, especially those derived from amines, for instance triethanolamine stearate; polyoxyethylenated fatty acid salts, especially those derived from amines or alkali metal salts, and mixtures thereof; phosphoric esters and salts thereof, such as DEA oleth-10 phosphate or monocetyl monopotassium phosphate sulfosuccinates, such as Disodium PEG-5 citrate lauryl sulfosuccinate and disodium ricinoleamido MEA sulfosuccinate; alkyl ether sulfates, such as sodium lauryl ether sulfate; isethionates; acylglutamates, such as disodium hydrogenated tallow glutamate, alkyl polyglucosides and mixtures thereof.

It is also possible to use one or more amphoteric surfactants, for instance N-acylamino acids such as N-alkylaminoacetates and disodium cocoamphodiacetate, and amine oxides, such as stearamine oxide, or alternatively silicone surfactants, for instance dimethicone copolyol phosphates.

The HEC can be substituted by other water thickeners such as water-soluble cellulose-based thickeners, guar gum, xanthan gum, carob gum, scleroglucan gum, gellan gum, rhamsan gum, karaya gum or carrageenan gum, alginates, maltodextrins, starch and its derivatives.

Formulation 4: Rinse off conditioner

Phase A

| | |
|---|---|
| HEC | 1.5 |
| Water | 91.9 |

Phase B

| | |
|---|---|
| Octodecyl Trimethyl Ammonium Chloride | 0.3 |
| Cetearyl Alcohol | 1.0 |
| COOH-Elastomer | 5.1 |

Phase C

| | |
|---|---|
| DMDM Hydantoin | 0.2 |

Procedure: Heat water to 80° C.; disperse HEC into water slowly under mixing; keep temperature at 80° C.; add Phase B to Phase A under mixing; and add Phase C when temperature is down to 45° C. and mix.

The HEC can be substituted by other water thickeners, such as those described in Formulation 3.

Formulation 5: Shampoo

Phase A

| | |
|---|---|
| Sodium Laureth Sulfate (28%) | 32.8 |
| Cocamide Diethanolamine | 5.9 |
| PEG-150 Pentaerythrityl Tetrastearate (and) PEG-6 Caprylic/Capric Glycerides (and) Water | 5.9 |
| Cocamidopropyl Betaine (30%) | 6.6 |
| Octodecyl Trimethyl Ammonium Chloride | 0.3 |
| Lauryl Glucoside | 4.7 |
| COOH-Elastomer | 4.7 |

Phase B

| | |
|---|---|
| Water | 39.3 |

Phase C

| | |
|---|---|
| DMDM Hydantoin | 0.2 |

Procedure: Heat Phase A to 65° C. and mix; heat Phase B to 45° C.; add Phase B to Phase A under mixing; cool Phase (A + B) to room temperature; and add Phase C to Phase (A + B) and mix.

In a similar fashion as the shower gel, alternative surfactants and thickening agents can be used.

Formulation 6: Water in silicone cream

Phase A

| | |
|---|---|
| PEG/PPG-19/19 Dimethicone (and) C13-16 Isoparaffin (and) C10-13 Isoparaffin | 4.2 |
| COOH-Elastomer | 15.8 |
| Soybean Oil | 5.3 |
| Phenyl Trimethicone (and) Dimethiconol | 2.1 |
| Cyclopentasiloxane | 2.1 |
| Caprylyl Methicone | 4.2 |
| Cyclopentasiloxane (and) Polypropylsilsesquioxane | 2.1 |

Phase B

| | |
|---|---|
| Water | 57.9 |
| Glycerin | 6.3 |
| Preservative & Fragrance | q.s. |

Procedure: Mix Phases A and B separately; drop Phase B into Phase A slowly; and mix Phase (A + B).

The silicone polyether (PEG/PPG 19/19 Dimethicone) can be either omitted or replaced by similar type of material as described in Formulation 2.

The silicone gum blend (Phenyltrimethicone and Dimethiconol) can be replaced by other types of gum blends where the carrier is a silicone oil, an organic oil or a blend of both. The silicone gum blend can also be replaced by silicone elastomer gels or elastomeric solid organopolysiloxanes enclosed in a fatty phase, where the elastomeric solid organopolysiloxane is at least partially cross-linked, examples of such being described in U.S. Pat. Nos. 4,987,169, 5,654,362, and 5,760,116; EP848029 and EP869142; and WO2007/109240, WO2007/109260, WO2007/109282, WO2009/006091, and WO2010/080755; which are incorporated by reference.

The volatile silicone oil (cyclopentasiloxane and Caprylyl methicone) can be replaced by any "volatile oil" corresponding to the following definition: oil (or non-aqueous medium) capable of evaporating on contact with the skin in less than one hour, at room temperature and atmospheric pressure. The volatile oil is a volatile cosmetic oil, which is liquid at room temperature, especially having a non-zero vapor pressure, at room temperature and atmospheric pressure, in particular having a vapor pressure ranging from 0.13-40,000, 1.3-13,000, 1.3-1,300, Pa.

The vegetable oil (soybean oil) can be replaced by a nonvolatile oil which can be hydrocarbon based, silicone based or vegetable based including esters and triglycerides. The film forming polymer (Polypropylsilsesquioxane) can be replaced by any other film former such as those described above.

| Formulation 7.1: Oil-in-water cream | |
|---|---|
| Phase A | |
| Glyceryl Stearate (and) Cetearyl Alcohol (and) Sodium Lauroyl Lactylate, Lecithin | 3.7 |
| Simmondsia Chinensis (Jojoba) Oil | 7.4 |
| Macadamia Ternifilia Seed Oil | 7.4 |
| COOH-Elastomer | 11.0 |
| Phase B | |
| Water | 51.5 |
| Glycerin | 2.2 |
| Phase C | |
| Glycerine (and) Water (and) Urea (and) Trehalose (and) Polyquaternium-51 (and) Sodium Hyaluronate | 5.1 |
| Bacopa monniera extract (and) Aqua (water) (and) PEG 8 (and) HEC | 2.2 |
| Butylene glycol (and) water (and) Laureth-3 HEC (and) acetyl dipeptide-1 cetyl ester | 2.9 |
| PEG-4 (and) lactic acid (and) kojic acid (and) butylene glycol (and) morus bombycis (and) arctostaphylos uva-ursi (and) glycyrrhiza glabra | 0.7 |
| Aqua (and) *acacia* senegal gum (and) hydrolysed soy protein (and) xanthan gum | 0.7 |
| Butylene glycol (and) water (and) Laureth-3 HEC (and) acetyl dipeptide-1 cetyl ester | 1.5 |
| Phase D | |
| Betaine | 1.5 |
| Water | 2.2 |
| Phase E | |
| Benzyl Alcohol (and) Methylchloroisothiazolinone (and) Methylisothiazolinone | 0.1 |
| Procedure: Heat Phase A to 80° C.; mix Phase B and heat to 80° C.; pour Phase A into Phase B under mixing; mix Phase (A + B) until homogenized lotion; keep mixing and cool mixture of Phase (A + B) to room temperature; add Phase C into Phase (A + B); mix Phase D and add Phase D to Phase (A + B + C); add Phase E to Phase (A + B + C + D); and keep mixing until homogenized cream. | |

| Formulation 7.2: Oil-in-water cream (2) | |
|---|---|
| Phase A | |
| Sodium Polyacrylate (and) Dimethicone (and) Cyclopentasiloxane (and) Trideceth-6 (and) PEG/PPG-18/18 Dimethicone | 2.1 |
| Caprylic/Capric Triglyceride | 7.1 |
| Simmondsia Chinensis Oil | 3.6 |
| Olive Oil | 2.1 |
| Bis-hydroxyethoxypropyl Dimethicone | 2.8 |
| Dimethicone (and) Dimethiconol | 2.1 |
| CI 77891 & Hydrogenated Lecithin | 1.1 |
| Phase B | |
| HEC | 0.2 |
| Water | 64.4 |
| L-ascorbic Acid | 0.2 |
| Glycerin | 1.6 |
| COOH-Elastomer | 12.5 |
| Benzyl Alcohol, methylchloroisothiazolinone, methylisothiazolinone | 0.2 |
| Procedure: Mix Phase A; heat water to 75° C. and disperse HEC into water under mixing; mix Phase B; add Phase B to Phase A under mixing; and keep mixing until homogenized cream. | |

| Formulation 7.3: Oil-in-water cream (3) | |
|---|---|
| Phase A | |
| Glyceryl Stearate (and) Cetearyl Alcohol (and) Sodium Lauroyl Lactylate, Lecithin | 4.0 |
| COOH-Elastomer | 6.0 |
| Caprylyl Methicone | 6.0 |
| Mineral Oil | 8.0 |
| Phase B | |
| Water | 69.8 |
| Glycerin | 6.0 |
| Phase C | |
| Benzyl Alcohol (and) Methylchloroisothiazolinone (and) Methylisothiazolinone | 0.2 |
| Procedure: Heat Phase A and to 80° C.; mix Phase B and heat to 80° C.; pour Phase A into Phase B under mixing; mix Phase (A + B) until homogenized lotion; keep mixing and cool mixture of Phase (A + B) to room temperature; add Phase C to Phase (A + B); and keep mixing until homogenized cream. | |

The thickening/emulsifying polymer dispersion (Sodium polyacrylate) can be replaced by cross-linked acrylamide polymers and copolymers, such as Sepigel 305 and by the carbomer families. The oils (Caprylic/Capric triglycerides, Olive oil and Jojoba oil) can be replaced by a nonvolatile oil which can be hydrocarbon based, silicone based or vegetable based including esters and triglycerides The pigment (CI 77891 (and) Hydrogenated Lecithin) can be replaced by any other pigment included in the following definitions:

The term "pigments" should be understood as meaning white or colored, mineral or organic particles of any form, which are insoluble in the physiological medium, and which are intended to color the composition. The term "nacres" should be understood as meaning iridescent particles of any form, produced especially by certain mollusks in their shell, or else synthesized.

The pigments may be white or colored, and mineral and/or organic. In addition, these pigments could be treated/coated by a wide range of chemicals.

| Formulation 8.1: Oil-in-water foundation | |
|---|---|
| Phase A | |
| Steareth-21 | 1.5 |
| Steareth-2 | 1.5 |
| Stearic Acid | 3.0 |
| Caprylic/Capric Triglyceride | 3.0 |
| Mineral Oil | 3.0 |
| Cyclopentasiloxane (and) Acrylates/ Polytrimethylsiloxymethacrylate Copolymer | 4.0 |
| Pigment (Titanium dioxide, Talc, Dimethicone) | 9.0 |
| COOH-Elastomer | 15.0 |
| Phase B | |
| HEC (2.5% solution) | 10.0 |
| Water | 41.8 |
| Bis-PEG-18 Methyl Ether Dimethyl Silane | 2.0 |
| Glycerin | 6.0 |
| Phase C | |
| Benzyl Alcohol, methylchloroisothiazolinone, methylisothiazolinone | 0.2 |
| Procedure: Mix Phase A and heat to 80° C.; heat water to 75° C. and disperse HEC into water under mixing; mix Phase B and keep temperature at 75° C.; add Phase A to Phase B under mixing; keep mixing until homogenized | |

Formulation 8.1: Oil-in-water foundation product and cool to 45° C.; and add Phase C to Phase (A + B) and mix.

Formulation 8.2: Oil-in-water foundation (2)

Phase A

| | |
|---|---|
| Glycerol monostearate | 3.0 |
| Stearic Acid | 3.0 |
| Caprylic/Capric Triglyceride | 3.0 |
| Mineral Oil | 3.0 |

Phase B

| | |
|---|---|
| Cyclopentasiloxane (and) Acrylates/ Polytrimethylsiloxymethacrylate Copolymer Pigment (Titanium | 4.0 9.0 |

Phase C

| | |
|---|---|
| Water | 51.8 |
| Glycerin | 8.0 |

Phase D

| | |
|---|---|
| COOH-Elastomer | 15.0 |

Phase E

| | |
|---|---|
| Phenoxyethanol (and) Methylparaben (and) Ethylparaben (and) Butylparaben (and) Propylparaben (and) Isobutylparaben | 0.2 |

Procedure: Mix Phase A and heat to 80° C.; mix Phase B and add to Phase A under mixing; keep temperature of Phase (A + B) at 75° C.; heat Phase C to 75° C.; add Phase (A + B) to Phase C under mixing; keep mixing until homogenized and cool to 45° C.; add Phase D to Phase (A + B + C) and mix; and add Phase E to Phase (A + B + C + D) and mix.

The nonionic emulsifiers blend (Steareth-2, Steareth-21 and Glyceryl Stearate (and) PEG-100 Stearate) can be replaced by any other oxyethylenated and/or oxypropylenated ethers (which may comprise from 1-150 oxyethylene and/or oxypropylene groups) of glycerol; oxyethylenated and/or oxypropylenated ethers (which may comprise from 1-150 oxyethylene and/or oxypropylene groups) of fatty alcohols (especially of a $C_8$-$C_{24}$ or $C_{12}$-$C_{18}$ alcohol), such as oxyethylenated cetearyl alcohol ether containing 30 oxyethylene groups (CTFA name Ceteareth-30) and the oxyethylenated ether of the mixture of $C_{12}$-$C_{15}$ fatty alcohols comprising 7 oxyethylene groups (CTFA name $C_{12}$-$C_{15}$ Pareth-7); fatty acid esters (especially of a $C_8$-$C_{24}$ or $C_{16}$-$C_{22}$ acid) of polyethylene glycol (which may comprise from 1-150 ethylene glycol units), such as PEG-50 stearate and PEG-40 monostearate; fatty acid esters (especially of a $C_8$-$C_{24}$ or $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate; glyceryl stearate polyethoxylated with 30 EO groups, glyceryl oleate polyethoxylated with 30 EO groups, glyceryl cocoate polyethoxylated with 30 EO groups, glyceryl isostearate polyethoxylated with 30 EO groups, and glyceryl laurate polyethoxylated with 30 EO groups; fatty acid esters (especially of a $C_8$-$C_{24}$ or $C_{16}$-$C_{22}$ acid) of oxyethylenated and/or oxypropylenated sorbitol ethers (which may comprise from 1-150 oxyethylene and/or oxypropylene groups), dimethicone copolyol; dimethicone copolyol benzoate; copolymers of propylene oxide and of ethylene oxide, also known as EO/PO polycondensates; and mixtures thereof; saccharide esters and ethers, such as sucrose stearate, sucrose cocoate and sorbitan stearate, and mixtures thereof, fatty acid esters (especially of a $C_8$-$C_{24}$ or $C_{16}$-$C_{22}$ acid) of polyols, especially of glycerol or of sorbitol, such as glyceryl stearate, glyceryl stearate, glyceryl laurate, polyglyceryl-2 stearate, sorbitan tristearate or glyceryl ricinoleate.

The stearic acid can be replaced by other waxes corresponding to the following definition: lipophilic compound that is solid at room temperature (25° C.), which undergoes a reversible solid/liquid change of state, and which has a melting point of ≥30° C., which may be up to 120° C. By bringing the wax to the liquid state (melting), it is possible to make it miscible with the oils that may be present and to form a microscopically homogeneous mixture, but on reducing the temperature of the mixture to room temperature, recrystallization of the wax in the oils of the mixture takes place.

The oils (Caprylic/Capric triglycerides and Mineral oil) can be replaced by a nonvolatile oil which can be hydrocarbon based, silicone based or vegetable based including esters and triglycerides The film forming polymer (Acrylates/Polytrimethylsiloxymethacrylate Copolymer) can be replaced by any other film former such as those described above. This film former can be delivered from either an oil media, aqueous media or in an emulsion form.

The pigment (CI 77891 (and) Hydrogenated Lecithin) can be replaced by any other pigment as described in Formulation 7.

Formulation 9: Loose powder

Phase A

| | |
|---|---|
| Talc | 68.0 |
| Titanium Dioxide | 12.0 |
| Pigment (CI 15850, triethoxycaprylysilane; CI 42090 & Triethoxycaprylylsilane; Iron oxides (and) hydrogenated lecithin) | 3.0 |
| HDI/Trimethylol Hexyllactone Cross-polymer (And) Silica | 5.0 |
| Dimethicone/Vinyldimethicone Cross-polymer (and) Silica | 1.0 |
| Mica | 1.5 |
| CI 77891 & CI 77491 & Mica & Triethoxycaprylylsilane | 1.0 |
| COOH-Elastomer | 5.5 |
| Dimethicone | 3.0 |

Procedure: Add component one by one to the pigment mixer; and mix all components.

The fillers (Talc, BPD 500, Mica and submica) can be replaced by the following other filler families: mineral or organic, of any form, platelet-shaped, spherical or oblong, irrespective of the crystallographic form (for example lamellar, cubic, hexagonal, orthorhombic, etc.) such as silica, kaolin, polyamide, poly-β-alanine powder and polyethylene powder, tetrafluoroethylene polymer (Teflon®) powders, lauroyllysine, starch, boron nitride, hollow polymer microspheres, or of acrylic acid copolymers and silicone resin microbeads, elastomeric polyorganosiloxane particles, elastomeric organopolysiloxane powder coated with silicone resin, especially with silsesquioxane resin, hybrid silicone powders functionalized with fluoroalkyl groups, phenyl groups, precipitated calcium carbonate, magnesium carbonate, magnesium hydrogen carbonate, hydroxyapatite, hollow silica microspheres, glass or ceramic microcapsules, and metal soaps for example zinc stearate, magnesium stearate, lithium stearate, zinc laurate or magnesium myristate, polymethyl methacrylate powders, polyurethane powder as well as fibers defined as the following: "fibre" or "fiber" should be understood as meaning an object of length L and diameter D such that L is very much greater than D, D being the diameter of the circle in which the cross section of the fibre is inscribed.

The pigments (Iron Oxides, TiO$_2$ and Covapealantique) can be replaced by any other pigment as described in Formulation 7. Silicone oil (dimethicone) can be replaced by a nonvolatile oil which can be hydrocarbon based, silicone based or vegetable based including esters and triglycerides.

| Formulation 10: Lip gloss | |
|---|---|
| Phase A | |
| Dimethicone | 15.0 |
| Cyclopentasiloxane (and) Dimethiconol | 39.9 |
| Phenyltrimethicone | 6.0 |
| Bis-hydroxyethoxypropyl Dimethicone | 12.0 |
| Dimethicone (and) Trimethylsiloxysilicate | 8.0 |
| Olive Oil | 2.0 |
| Ethylhexyl Salicylate | 6.0 |
| COOH-Elastomer | 11.0 |
| Phase B | |
| Silica Silylate | 0.3 |

Procedure: Add components in Phase A one by one in order under mixing; mix Phase A at 75° C.; add Phase B into Phase A under mixing; and mix Phase (A + B).

Silicone and natural oils (Dimethicone, Phenyltrimethicone, Bis-hydroxyethoxypropyl Dimethicone, olive oil) can be replaced by a nonvolatile oil which can be hydrocarbon based, silicone based or vegetable based including esters and triglycerides.

Silicone gum blend (Cyclopentasiloxane and Dimethiconol) can be replaced by other gum blends or elastomer blends as described in Formulation 6. Silicone resin (Trimethylsiloxysilicate) can be replaced by other film formers as described in Formulation 8. Silica (silica silylate) can be replaced by other fillers as described in Formulation 9. The pigments (Iron Oxides, TiO$_2$) can be replaced by any other pigment as described in Formulation 7. Sunscreen (Ethylhexyl Salicylate) can be replaced by any other liquid organic sunscreens, such as those described above.

| Formulation 11.1: Blemish treatment paste | |
|---|---|
| Phase A | |
| Stearyl Dimethicone | 10.0 |
| C30-45 Alkyldimethylsilyl polypropylsilsesquioxane | 12.0 |
| Phase B | |
| Caprylyl Methicone | 25.0 |
| Bis-hydroxyethoxypropyl Dimethicone | 10.0 |
| Dimethicone/Vinyldimethicone Cross-polymer (and) Silica | 10.0 |
| Titanium Dioxide | 13.0 |
| Castor Oil, CI19140 | 10.0 |
| COOH-Elastomer | 10.0 |

Procedure: Heat Phase A to 70° C.; add components in Phase B one by one to Phase A under mixing and keep temperature; mix Phase (A + B); and pour into package bottle and cool to room temperature.

| Formulation 11.2: Blemish treatment paste (2) | |
|---|---|
| Phase A | |
| Stearyl Dimethicone | 10.0 |
| C$_{30}$-C$_{45}$ Alkyldimethylsilyl polypropylsilsesquioxane | 12.0 |
| Phase B | |
| Bis-hydroxyethoxypropyl Dimethicone | 10.0 |
| Dimethicone/Vinyldimethicone Cross-polymer (and) Silica | 10.0 |
| Titanium Dioxide | 13.0 |
| Castor Oil, CI19140 | 10.0 |
| Phase C | |
| Water | 25.0 |
| COOH-Elastomer | 10.0 |

Procedure: Heat Phase A to 70° C.; add components in Phase B one by one to Phase A under mixing and keep temperature; mix Phase (A + B); mix Phase C; add Phase C to Phase (A + B) under mixing; and cool to room temperature.

Silicone oils (Caprylyl Methicone, Bis-hydroxyethoxypropyl Dimethicone) can be replaced by a volatile and nonvolatile oils which can be hydrocarbon based, silicone based or vegetable based including esters and triglycerides. Silicone wax (C$_{30}$-C$_{45}$ Alkyldimethylsilyl Polypropylsilsesquioxane) can be replaced by other waxes as described in Formulation 8.

Alkyl methyl Silicone (Stearyl Dimethicone) can be replaced by any other alkylmethylsiloxanes, siloxane polymers generally having the formula Me$_3$SiO[Me$_2$SiO]$_y$[MeRSiO]$_z$SiMe$_3$, in which R is a hydrocarbon group containing 6-30 carbon atoms, Me represents methyl, and the degree of polymerization (DP), i.e., the sum of y and z is 3-50. These alkylmethysiloxanes can be volatile, nonvolatile and solid at room temperature. The pigments (Iron Oxides, TiO$_2$) can be replaced by any other pigment either pure or pre-dispersed in a carrier as described in Formulation 7.

| Formulation 12: Lipstick | |
|---|---|
| Phase A | |
| Ozocerite | 4.0 |
| Carnauba Wax | 11.0 |
| Petrolatum | 4.0 |
| Beeswax | 4.0 |
| Lanolin | 2.0 |
| Candelilla Wax | 1.0 |
| Microcrystalline Wax | 1.0 |
| Euphorbia Cerifera & Isopropyl Palmitate & Ozokerite & Cetearyl Ethylhexanoate & Isostearyl Alcohol & Copernicia Cerifera & Myristyl Lactate & Synthetic Beeswax & BHT | 10.0 |
| C$_{30}$-C$_{45}$ Alkyldimethylsilyl polypropylsilsesquioxane | 5.0 |
| COOH-Elastomer | 19.0 |
| Phase B | |
| Hydrogenated dimer Dilinoleyl/Dimethylcarbonate Copolymer | 14.0 |
| Oleyl Alcohol | 8.0 |
| Caprylyl Methicone | 9.0 |
| Pigment (Iron Oxide, CI331700, CI 77891, CI 73360, Titanium Dioxide) | 10.0 |

Procedure: Using pigment mixer mix all pigments; melt all components in Phase A and mix; mix Phase B; add Phase B to Phase A and mix; pour Phase (A + B) into lipstick mold; put lipstick mold into refrigerator for 15 minutes; and take lipstick out of mold.

Waxes (Ozokerite, Carnauba wax, Beeswax, Candelilla wax, Microcrystalline and C$_{30}$-C$_{45}$ methicone) can be replaced by other waxes as described in Formulation 8. Oleyl alcohol can also be replaced by other fatty alcohols, such as stearyl alcohol, cetyl alcohol, etc. Film forming polymer (Hydrogenated dimer Dilinoleyl/Dimethylcarbonate Copolymer) can be replaced by any other film former, such as those described above. The pigments (Iron Oxides) can be replaced by any other pigment as described in Formulation 7.

| Formulation 13: W/O foundation | |
|---|---|
| Phase A | |
| Bis-Isobutyl PEG/PPG-10/7/Dimethicone Copolymer | 2.0 |
| $C_{30}$-$C_{45}$ Alkyldimethylsilyl polypropylsilsesquioxane | 2.0 |
| COOH-Elastomer | 20.0 |
| Trimethylsiloxy silicate (and) Polypropyl silsesquioxane | 1.0 |
| Isododecane | 1.0 |
| Phase B | |
| Water | 46.0 |
| Glycerin | 15.0 |
| Sodium Chloride | 1.0 |
| Phase C | |
| Caprylyl Methicone | 5.0 |
| Pigment (Iron Oxide, Titanium Dioxide) | 7.0 |
| Procedure: Using a pigment mixer mix all pigments; mix Phase C; mix Phase B; heat Phase A to melt wax and mix Phase A; add Phase C to Phase A and mix; drop Phase B into Phase (A + C) slowly under mixing; and mix foundation until homogenized. | |

The silicone polyether (Bis-Isobutyl PEG/PPG-10/7/Dimethicone Copolymer) that can be either omitted or replaced by similar type of material as described in the Formulation 2. Silicone wax ($C_{30}$-$C_{45}$ Alkyldimethylsilyl Polypropylsilsesquioxane) can be replaced by other waxes as described in Formulation 8.

Film forming polymer (Trimethylsiloxysilicate and polypropylsilsesquioxane) can be replaced by any other film former such as those described above. The volatile silicone oil (Caprylyl methicone) can be replaced by any "volatile oil" as described in Formulation 6. The pigments (Iron Oxides) can be replaced by any other pigment as described in Formulation 7.

| Formulation 14: Clear gel | |
|---|---|
| Phase A | |
| Glycerin | 42.1 |
| Water | 27.0 |
| Phase B | |
| COOH-Elastomer | 30.9 |
| Procedure: Mix phase A; and add Phase A to Phase B and mix. | |

This clear gel is obtained by matching the refractive index of the water phase to the one of the silicone organic blend elastomer gel carrier with the help of glycerin. Other glycols, such as propylene glycol, butylene glycol, dipropylene glycol or even ethanol or isopropyl alcohol can be used. Also, any other water soluble components impacting the Refractive index of the aqueous phase can also be used such as aluminum salt, sugar, etc.

| Formulation 15: Anhydrous sun care gel | |
|---|---|
| Phase A | |
| COOH-Elastomer | 67.4 |
| Phase B | |
| Ethylhexyl Methoxycinnamate | 7.5 |
| Ethylhexyl Salicylate | 5.0 |
| Capryllic/Capric Triglyceride | 8.0 |
| Dicaprylyl Carbonate | 12.0 |
| Phase C | |
| Silica Silylate | 0.1 |
| Procedure: Mix all components in Phase B; add Phase B to Phase A under mixing; and add Phase C to Phase (A + B) and mix. | |

The oil (Caprylic/Capric triglycerides) can be replaced by a nonvolatile oil which can be hydrocarbon based, silicone based or vegetable based including esters and triglycerides. Silica (silica silylate) can be replaced by other fillers as described in Formulation 9. Sunscreens (Ethylhexyl salycilate and Ethylhexyl Methoxycinnamate) can be replaced by any other liquid organic sunscreens.

The different formulations described above illustrate the great versatility and ease of formulating of the cross-linked composition (e.g. COOH-elastomer), overcoming the limitations of conventional elastomers gels by providing ideal balance between compatibility with the major components used in cosmetic formulations and the unique texture and feel.

Various specific embodiments follow hereafter. In various embodiments, component C) (i.e., the compound having an aliphatic unsaturated hydrocarbon group and at least one carboxyl group or a carboxyl group precursor) comprises ASA, trimethylsilyl undecylenate, or a combination thereof. In certain embodiments, W of the cross-linked composition comprises: i) an organic group, a siloxane group, or an organosiloxane group; or ii) at least one of a hydrocarbylene, heterohydrocarbylene, or organoheterylene group. In certain embodiments, each of $R^1$, $R^2$, and $R^4$ of the cross-linked composition is an independently selected monovalent organic group having 1 to 30 carbon atoms.

In various embodiments, the cross-linked composition (e.g. COOH-Elastomer) is reacted with one of the at least one cosmetic component. In certain embodiments, the cosmetic component of the cosmetic composition is selected from emollients, waxes, moisturizers, surface active materials, thickeners, water phase stabilizing agents, pH controlling agents, preservatives and cosmetic biocides, sebum absorbants, sebum control agents, vegetable extracts, botanical extracts, vitamins, proteins and their derivatives, aminoacids and their derivatives, pigments, colorants, fillers, silicone conditioning agents, cationic conditioning agents, UV absorbers, sunscreen agents, antidandruff agents, antiperspirant agents, deodorant agents, skin protectants, hair dyes, nail care components, fragrances, perfume, antioxidants, oxidizing agents, reducing agents, propellant gases, fatty alcohols, color care additives, pearlising agents, chelating agents, film formers, styling agents, ceramides, suspending agents, and mixtures thereof. In various embodiments, the cosmetic composition in the form of a cream, a gel, a powder (free flowing powder or pressed), a paste, a solid, a freely pourable liquid, or an aerosol. In certain embodiments, the cosmetic composition is a lipstick, a foundation, a primer, a body cream, a face cream, a hair coloring product, a mascara, or a blush. Moreover, in various embodiments, the cosmetic composition is in the form of a shampoo, a cream, a rinse-off conditioner, a leave-in conditioner, or a gel.

The terms "comprising" or "comprise" are used herein in their broadest sense to mean and encompass the notions of "including", "include", "consist(ing) essentially of", and "consist(ing) of". The use of "for example", "e.g.", "such as", and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-10, ±0-5, or +0-2.5, % of the numerical values. Further, The term "about" applies to both numerical values when associated with a range of values. Moreover, the term "about" may apply to numerical values even when not explicitly stated.

The term "ambient temperature" or "room temperature" as used herein refers to a temperature of from about 20-30, ° C. Usually, "room temperature" ranges from about 20-25, ° C. All viscosity measurements referred to herein were measured at 25° C. unless otherwise indicated. Generally, as used herein a hyphen "-" or dash "-" in a range of values is "to" or "through"; a ">" is "above" or "greater-than"; a "≥" is "at least" or "greater-than or equal to"; a "<" is "below" or "less-than"; and a "5" is "at most" or "less-than or equal to".

The term "branched" as used herein describes a polymer with >2 end groups. The term "substituted" as used in relation to another group, for example, a hydrocarbon group, means, unless indicated otherwise, one or more hydrogen atoms in the hydrocarbon group has been replaced with another substituent. Examples of such substituents include, but are not limited to, halogen atoms, such as chlorine, fluorine, bromine, and iodine; halogen atom containing groups, such as chloromethyl, perfluorobutyl, trifluoroethyl, and nonafluorohexyl; oxygen atoms; oxygen atom containing groups, such as (meth)acrylic and carboxyl; nitrogen atoms; nitrogen atom containing groups, such as amines, amino-functional groups, amido-functional groups, and cyano-functional groups; sulphur atoms; and sulphur atom containing groups, such as mercapto groups.

On an individual basis, each of the aforementioned applications for patent, patents, and/or patent application publications, is expressly incorporated herein by reference in its entirety in one or more non-limiting embodiments.

One or more of the values described above may vary by ±5%, ±10%, ±15%, ±20%, ±25%, etc. so long as the variance remains within the scope of this disclosure. Unexpected results may be obtained from each member of a Markush group independent from all other members. Each member may be relied upon individually and/or in combination and provides adequate support for specific embodiments within the scope of the appended claims. The subject matter of all combinations of independent and dependent claims, both single and multiple dependent, is herein expressly contemplated. This disclosure is illustrative including words of description rather than of limitation. Many modifications and variations of the present disclosure are possible in light of the above teachings, and the disclosure may be practiced otherwise than as specifically described herein.

The invention claimed is:

1. A cross-linked composition comprising the reaction product of:
   A) an organohydrogensiloxane comprising siloxy units of average formula (I);

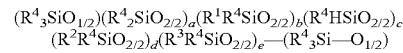

where each of $R^1$ and $R^2$ is an independently selected hydrogen atom or a substituted or unsubstituted hydrocarbyl group, $R^3$ is a group having at least one carboxyl group or a precursor thereof selected from an anhydride group and a capped carboxyl group, each $R^4$ is an independently selected substituted or unsubstituted hydrocarbyl group, $a \geq 0$, $b \geq 0$, $c \geq 1$, $d \geq 0$, and $e \geq 1$; and
   B) a cross-linker having at least two aliphatic unsaturated hydrocarbon groups;
   in the presence of
   a hydrosilylation catalyst.

2. A cosmetic composition comprising:
   (I) a cross-linked composition; and
   (II) at least one cosmetic component;
   optionally in a cosmetically acceptable medium;
   wherein the cross-linked composition is as set forth in claim 1.

3. The composition as set forth in claim 1, wherein said cross-linked composition comprises the further reaction product of C2) water, an alcohol, or a combination thereof.

4. The composition as set forth in claim 1, wherein component B) is of formula (III): $R^5$—Y—$R^5$; where $R^5$ is a monovalent unsaturated aliphatic hydrocarbon group having 2 to 12 carbon atoms and Y is a divalent organic group, divalent siloxane group, or divalent organosiloxane group.

5. The composition as set forth in claim 1, said cross-linked composition being of the following general formula (II):

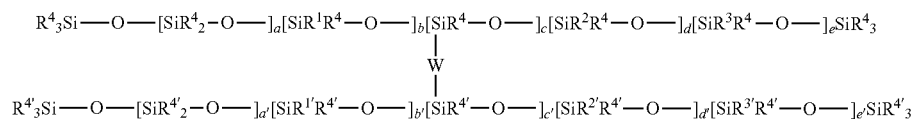

where W is a divalent group, each of $R^1$, $R^{1'}$, $R^2$, $R^{2'}$, $R^4$, and $R^{4'}$ is an independently selected substituted or unsubstituted hydrocarbyl group, each of $R^3$ and $R^{3'}$ is independently a group having at least one carboxyl group or a precursor thereof, $a \geq 0$, $a' \geq 0$, $b \geq 0$, $b' \geq 0$, $c \geq 1$, $c' \geq 1$, $d \geq 0$, $d' \geq 0$, $e \geq 1$, and $e' \geq 1$.

6. The composition as set forth in claim 1, wherein:
   i) $R^3$ has a terminal carboxyl group; or
   ii) $R^3$ has a terminal carboxyl group precursor selected from an anhydride group or a capped carboxyl group; or
   iii) $R^3$ is a derivative of allyl succinic anhydride (ASA) or trimethylsilyl undecylenate.

7. The composition as set forth in claim 1, wherein:
   i) the sum of $a+b+c+d+e$ is an integer selected from 4 to 2,000; and/or
   ii) $10 \leq a \leq 500$, $0 \leq b \leq 100$, $1 \leq c \leq 100$, $0 \leq d \leq 100$, and $1 \leq e \leq 100$; and/or iii) $R^1$ is a methyl group, $R^2$ is an aliphatic or aromatic group having from 1 to 12 carbon atoms, and $R^4$ is $R^1$.

8. A method of forming a cross-linked composition, said method comprising the steps of:

providing A) an organohydrogensiloxane comprising siloxy units of average formula (I);

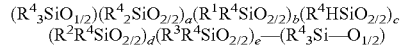
$(R^4{}_3SiO_{1/2})(R^4{}_2SiO_{2/2})_a(R^1R^4SiO_{2/2})_b(R^4HSiO_{2/2})_c$
$(R^2R^4SiO_{2/2})_d(R^3R^4SiO_{2/2})_e\mathord{-\!\!-}(R^4{}_3Si\mathord{-\!\!-}O_{1/2})$ where each of $R^1$ and $R^2$ is an independently selected hydrogen atom or a substituted or unsubstituted hydrocarbyl group, $R^3$ is a group having at least one carboxyl group or a precursor thereof selected from an anhydride group and a capped carboxyl group, each $R^4$ is an independently selected substituted or unsubstituted hydrocarbyl group, $a \geq 0$, $b \geq 0$, $c \geq 1$, $d \geq 0$, and $e \geq 1$;

providing B) a cross-linker having at least two aliphatic unsaturated hydrocarbon groups; and combining components A) and B) in the presence of a hydrosilylation catalyst to form the cross-linked composition;

wherein the cross-linked composition is at set forth in claim 1.

9. The method as set forth in claim 8, further comprising the steps of:

providing D) water, an alcohol, or a combination thereof; and reacting the cross-linked composition and component D) to further form the cross-linked composition.

10. The method as set forth in claim 8, further comprising the step of:

providing C2) water, an alcohol, or a combination thereof; and reacting $R^3$ and component C2) to further form the cross-linked composition.

11. The composition as set forth in claim 3, wherein $R^3$ is a derivative of allyl succinic anhydride (ASA).

12. The composition as set forth in claim 3, wherein $R^3$ is a derivative of trimethylsilyl undecylenate.

13. The method as set forth in claim 10, wherein $R^3$ is a derivative of allyl succinic anhydride (ASA) or trimethylsilyl undecylenate.

14. The cosmetic composition as set forth in claim 2, further defined as a personal care composition and/or a composition for the care of keratinous substrates.

15. The cosmetic composition as set forth in claim 2, wherein the cosmetically acceptable medium is present.

* * * * *